(12) United States Patent
Kamei

(10) Patent No.: US 9,023,830 B2
(45) Date of Patent: May 5, 2015

(54) COSMETIC

(71) Applicant: Shin-Etsu Chemical Co., Ltd., Tokyo (JP)

(72) Inventor: Masanao Kamei, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 127 days.

(21) Appl. No.: 13/848,473

(22) Filed: Mar. 21, 2013

(65) Prior Publication Data

US 2013/0267478 A1 Oct. 10, 2013

(30) Foreign Application Priority Data

Apr. 4, 2012 (JP) ................................. 2012-085935

(51) Int. Cl.
| | |
|---|---|
| *A61K 8/73* | (2006.01) |
| *A61Q 19/00* | (2006.01) |
| *A61Q 1/02* | (2006.01) |
| *A61Q 1/06* | (2006.01) |
| *A61Q 1/08* | (2006.01) |
| *A61Q 1/10* | (2006.01) |
| *A61Q 1/12* | (2006.01) |
| *A61Q 3/02* | (2006.01) |
| *A61Q 5/06* | (2006.01) |
| *A61Q 5/12* | (2006.01) |
| *A61Q 15/00* | (2006.01) |
| *A61Q 17/04* | (2006.01) |
| *A61Q 19/04* | (2006.01) |
| *A61Q 19/08* | (2006.01) |
| *A61Q 19/10* | (2006.01) |

(52) U.S. Cl.
CPC . *A61K 8/73* (2013.01); *A61K 8/731* (2013.01); *A61Q 19/00* (2013.01); *A61Q 1/02* (2013.01); *A61Q 1/06* (2013.01); *A61Q 1/08* (2013.01); *A61Q 1/10* (2013.01); *A61Q 1/12* (2013.01); *A61Q 3/02* (2013.01); *A61Q 5/06* (2013.01); *A61Q 5/12* (2013.01); *A61Q 15/00* (2013.01); *A61Q 17/04* (2013.01); *A61Q 19/04* (2013.01); *A61Q 19/08* (2013.01); *A61Q 19/10* (2013.01); *A61K 2800/10* (2013.01)

(58) Field of Classification Search
CPC ..... A61K 8/73; A61K 2800/10; A61Q 19/00; A61Q 1/02
USPC .................................. 514/57, 54; 536/32, 53
See application file for complete search history.

(56) References Cited

U.S. PATENT DOCUMENTS

| | | | |
|---|---|---|---|
| 5,583,244 A | 12/1996 | Uchida et al. | |
| 5,891,977 A | 4/1999 | Dietz et al. | |
| 2004/0248761 A1* | 12/2004 | Booten et al. .................. | 510/470 |
| 2005/0250904 A1 | 11/2005 | Okawa et al. | |

FOREIGN PATENT DOCUMENTS

| | | |
|---|---|---|
| JP | A-62-68820 | 3/1987 |
| JP | A-8-134103 | 5/1996 |
| JP | A-10-29910 | 2/1998 |
| JP | A-10-29921 | 2/1998 |
| JP | A-10-330489 | 12/1998 |
| JP | A-2004-156004 | 6/2004 |

* cited by examiner

*Primary Examiner* — Brandon Fetterolf
*Assistant Examiner* — Yih-Horng Shiao
(74) *Attorney, Agent, or Firm* — Oliff PLC

(57) ABSTRACT

There is disclosed a cosmetic comprises a sugar compound obtained by reacting a hydroxyl group of a saccharide, an isocyanate group-containing organopolysiloxane represented by the following general formula (1), and an isocyanate group-containing organic compound represented by the following general formula (2).

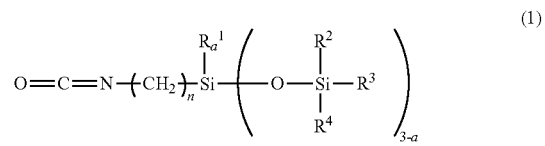

As a result, there is provided a cosmetic excellent in cosmetic sustainability and storage stability that can improve such undesirable feelings of use as insufficient spreadability and stickiness, improve the solubility to not only a non-polar oil such as a silicone oil and a light liquid paraffin, but also a polar oil such as a UV-absorber, an ester oil, and a natural animal and vegetable oil, provides non-stickiness with a cosmetic containing the polar oil, and prevent adhesion of the cosmetic to clothes (secondary adhesion).

20 Claims, No Drawings

COSMETIC

BACKGROUND OF THE INVENTION

1. Field of the Invention

The present invention relates to a cosmetic comprising an organopolysiloxane-containing sugar compound.

2. Description of the Related Art

An organopolysiloxane-containing sugar compound obtained from an organopolysiloxane having a saccharide and a reactive group has been conventionally obtained by known methods: 1) a method for subjecting to ring-opening reaction a primary amino group-containing organopolysiloxane and a lactonic compound in which an aldonic acid or an uronic acid is cyclodehydrated (Patent Document 1); 2) a method for reacting an isocyanate group-containing organopolysiloxane and a hydroxyl group of a pullulan (Patent Document 2); 3) a method for reacting an epoxy-functional siloxane and an amino-functional sugar derivative (Patent Document 3); and 4) a method for producing a half-ester copolymer by reacting an organopolysiloxane having an anhydrous carboxylic acid group and a polysaccharide in the presence of an aprotic organic solvent (Patent Document 4).

The Patent Document 2 discloses a siliconized pullulan obtained by reacting a sugar compound pullulan and an isocyanate group-containing organopolysiloxane. In addition, Patent Document 5 and Patent Document 6 disclose a cosmetic containing the siliconized polysaccharide compound. The cosmetic is excellent in water resistance, oil resistance, secondary adhesion-free effect, and feeling of use, as well as biodegradability and biological safety.

CITATION LIST

Patent Literature

PATENT DOCUMENT 1: Japanese Examined Patent Publication No. S62-68820
PATENT DOCUMENT 2: Japanese Examined Patent Publication No. H8-134103
PATENT DOCUMENT 3: Japanese Examined Patent Publication No. H10-330489
PATENT DOCUMENT 4: Japanese Examined Patent Publication No. 2004-156004
PATENT DOCUMENT 5: Japanese Examined Patent Publications No. H10-29910
PATENT DOCUMENT 6: Japanese Examined Patent Publications No. H10-29921

SUMMARY OF THE INVENTION

Unfortunately, the above conventional techniques have problematic feelings of use such as undesirable spreadability and stickiness.

The siliconized polysaccharide compound dissolves in a non-polar oil material such as a silicone oil and a light liquid paraffin of a low molecular weight to be blended into a cosmetic. However, siliconization is not enough to cause a complete dissolution in a polar oil, thereby achieving insufficient temporal stability and cosmetic sustainability in the cosmetic containing the polar oil.

The present invention was made to solve the problems mentioned above, and was intended to provide a cosmetic excellent in cosmetic sustainability and storage stability that can improve such undesirable feelings of use as insufficient spreadability and stickiness, improve the solubility to not only non-polar oil such as a silicone oil and a light liquid paraffin, but also a polar oil such as a UV-absorber, and an ester oil, a natural animal and vegetable oil, provides non-stickiness with a cosmetic containing the polar oil, and prevent adhesion of the cosmetic to clothes (secondary adhesion).

To solve the problems as mentioned above, the present invention provides a cosmetic comprising a sugar compound obtained by reacting a hydroxyl group of a saccharide, an isocyanate group-containing organopolysiloxane represented by the following general formula (1), and an isocyanate group-containing organic compound represented by the following general formula (2),

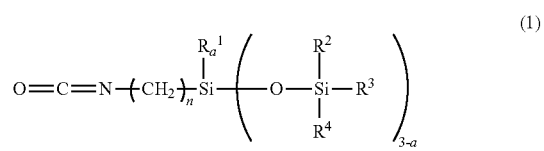

wherein $R^1$, $R^2$, $R^3$, and $R^4$ independently represent a group selected from an alkyl group having 1 to 8 carbon atoms, a fluorine-substituted alkyl group having 1 to 8 carbon atoms, and an aryl group having 6 to 12 carbon atoms, with "n" representing an integer of 1 to 10 and "a" representing an integer of 0 to 3,

wherein $R^5$ represents a group selected from an alkyl group having 3 to 30 carbon atoms, an aryl group having 6 to 30 carbon atoms, an aralkyl group having 6 to 30 carbon atoms, and an organic group represented by the following general formula (3),

wherein $R^6$ represents a divalent hydrocarbon group having 2 to 20 carbon atoms; and $R^7$ represents an alkyl group having 1 to 30 carbon atoms, with "X" representing a group represented by —NHCONH— or NHCOO—.

The cosmetic of the present invention is excellent in such feelings of use as spreadability and non-stickiness. In addition, due to a film-forming property in the cosmetic, a cosmetic even containing a polar oil is excellent in cosmetic sustainability and storage stability that provides non-stickiness and prevent adhesion of the cosmetic to clothes (secondary adhesion).

The sugar compound preferably is reacted with the isocyanate group-containing organopolysiloxane and the isocyanate group-containing organic compound, with the molar ratio being in the range of 0.03 to 0.7 per mole of a hydroxyl group of the saccharide.

A sugar compound thus reacted therewith with such a molar ratio can assuredly provide more excellent feelings of use with a cosmetic containing the same. By controlling the molar ratio within the above range, an appropriate type of sugar compound can be selected, depending on an oil material used.

The saccharide is preferably a pullulan or a cellulose.

With effective properties such as coating, film forming and strong toughness in a pullulan and a cellulose, a cosmetic containing a sugar compound obtained from the saccharide is particularly excellent in secondary adhesion-preventing effect and cosmetic sustainability.

It is preferable that, "n" be 3, and $R^1$, $R^2$, $R^3$ and $R^4$ represent a methyl group in the general formula (1).

The cosmetic comprising a sugar compound obtained from the isocyanate group-containing organopolysiloxane exhibits excellent feelings of use such as favorable spreadability and non-stickiness.

$R^5$ is preferably an alkyl group having 3 to 30 carbon atoms in the general formula (2).

The cosmetic comprising a sugar compound obtained from the isocyanate group-containing organic compound is excellent in cosmetic sustainability and stability that can improve the solubility to not only a non-polar oil such as a silicone oil and a light liquid paraffin, but also a polar oil such as a UV-absorber, an ester oil, and a natural animal and vegetable oil.

The cosmetic preferably contains the sugar compound, with the amount thereof being 0.05 to 40% by mass, relative to the total amount of the cosmetic.

Accordingly, the cosmetic is particularly excellent in cosmetic storage stability and sustainability.

The cosmetic of the present invention may further contain water and be in the form of emulsion.

The cosmetic of the present invention can be in the form of emulsion suitable for each purpose.

Moreover, the cosmetic of the present invention may contain any of a silicone oil, a hydrocarbon oil, a glycol, an ester oil, a glyceride oil, a UV-absorber, and a mixture thereof.

The sugar compound in the cosmetic of the present invention is excellent in cosmetic sustainability and storage stability that can improve the solubility to not only a non-polar oil such as a silicone oil, but also a polar oil such as a UV-absorber and an ester oil, provides non-stickiness with a cosmetic containing the non-polar oil and the polar oil, and prevent adhesion of the cosmetic to clothes (secondary adhesion).

In addition, the cosmetic may contain a powder and be in the form of a liquid, a paste, or a solid, with the powder being dispersed therein.

The cosmetic of the present invention is excellent in powder dispersion stability due to no change in powder aggregation, even with a powder therein. The cosmetic can be used in various applications from favorable handleability in the form of any of a liquid, a paste or a solid.

Effects of Invention

As explained above, the cosmetic of the present invention is excellent in cosmetic sustainability and storage stability that can improve such undesirable feelings of use as insufficient spreadability and stickiness, improve the solubility to not only a non-polar oil such as a silicone oil and a light liquid paraffin, but also a polar oil such as a UV-absorber, an ester oil, and a natural animal and vegetable oil, provides non-stickiness with a cosmetic containing the polar oil, and prevent adhesion of the cosmetic to clothes (secondary adhesion). The cosmetic can be produced in a variety of forms and configurations, and be used in various applications in a significantly useful manner.

DESCRIPTION OF THE PREFERRED EMBODIMENTS

The present invention will be described in more detail.

As described above, a cosmetic comprising a conventional siliconized sugar compound exhibits unfavorable feelings of use, and problems with temporal stability and cosmetic sustainability from an oil material used in a cosmetic.

Inventor of the present invention carried out an extensive investigation on the problems mentioned above, and found that a sugar compound obtained by reacting a hydroxyl group of a saccharide, a specific isocyanate group-containing organopolysiloxane and an isocyanate group-containing organic compound is excellent in the solubility to not only a non-polar oil, but also a polar oil, and specifically, if the sugar compound is contained in a cosmetic, the cosmetic is excellent in cosmetic sustainability and storage stability that can provide favorable feelings of use and non-stickiness, and prevent adhesion of the cosmetic to clothes (secondary adhesion); and as a result, the present invention could be accomplished.

Accordingly, the cosmetic of the present invention comprises a sugar compound obtained by reacting a hydroxyl group of a saccharide, an isocyanate group-containing organopolysiloxane represented by the following general formula (1), and an isocyanate group-containing organic compound represented by the following general formula (2),

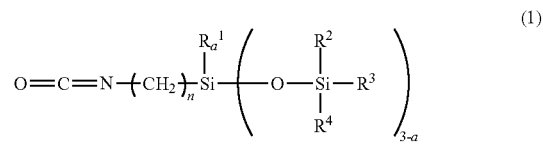

(1)

wherein $R^1$, $R^2$, $R^3$, and $R^4$ independently represent a group selected from an alkyl group having 1 to 8 carbon atoms, a fluorine-substituted alkyl group having 1 to 8 carbon atoms, and an aryl group having 6 to 12 carbon atoms, with "n" representing an integer of 1 to 10 and "a" representing an integer of 0 to 3,

$$O=C=N-R^5 \qquad (2)$$

wherein $R^5$ represents a group selected from an alkyl group having 3 to 30 carbon atoms, an aryl group having 6 to 30 carbon atoms, an aralkyl group having 6 to 30 carbon atoms, and an organic group represented by the following general formula (3),

$$-R^6-X-R^7 \qquad (3)$$

wherein, $R^6$ represents a divalent hydrocarbon group having 2 to 20 carbon atoms; $R^7$ represents an alkyl group having 1 to 30 carbon atoms, with "X" representing a group represented by —NHCONH— or NHCOO—.

As to the sugar compound to be blended into the cosmetic of the present invention, illustrative example of a known saccharide includes pullulan, cellulose, chitin, chitosan, starch, mannan, hyaluronic acid, and a derivative thereof, by means of, for example, methylation, ethylation, oxyalkylene addition such as ethylene oxide and propylene oxide, acylation, cationization, and so on. Among these are pullulan and cellulose preferably used. The molecular weight of a saccharide is preferably in the range of 500 to 5,000,000, and more preferably 30,000 to 400,000.

Illustrative example of the isocyanate group-containing organopolysiloxane includes the one represented by the above general formula (1). In the above general formula (1), $R^1$, $R^2$, $R^3$, and $R^4$ represent a group selected from an alkyl group having 1 to 8 carbon atoms, a fluorine-substituted alkyl group having 1 to 8 carbon atoms, and an aryl group having 6 to 12 carbon atoms, specifically an alkyl group such as a methyl group, an ethyl group, a propyl group, a butyl group, a pentyl group, a hexyl group, a heptyl group, and an octyl group; a cycloalkyl group such as a cyclopentyl group and a cyclohexyl group; an aryl group such as a phenyl group and a tolyl group; an aralkyl group such as a benzyl group and a phenethyl group; and a fluorine-substituted alkyl group such as a trifluoropropyl group and a heptadecafluorodecyl group, and preferably used is an alkyl group having 1 to 8 carbon atoms, or a phenyl group, and more preferably a methyl group.

It is preferable that "n" be an integer of 1 to 10, and more preferably 3.

"a" is an integer of 0 to 3.

Specific example of the isocyanate group-containing organopolysiloxane represented by the above general formula (1) includes the following ones.

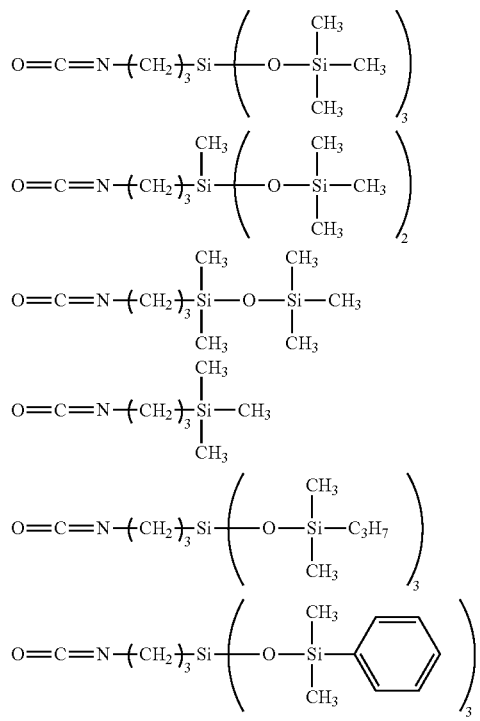

Illustrative example of the isocyanate group-containing organic compound includes the one represented by the above general formula (2). $R^5$ in the above general formula (2) represents a group selected from an alkyl group having 3 to 30 carbon atoms, specifically an alkyl group such as a propyl group, a butyl group, a pentyl group, a hexyl group, a heptyl group, an octyl group, a stearyl group, and a bephenyl group; a cycloalkyl group such as a cyclopentyl group and a cyclohexyl group; an aryl group having 6 to 30 carbon atoms, specifically an aryl group such as a phenyl group and a tolyl group; an aralkyl group having 6 to 30 carbon atoms, specifically an aralkyl group such as a benzyl group and a phenethyl group; and an organic group represented by the above general formula (3).

$R^6$ in the above general formula (3) represents a divalent hydrocarbon group having 2 to 20 carbon atoms, $R^7$ represents an alkyl group having 1 to 30 carbon atoms, X represents a group selected from —NHCOO— or NHCONH—. $R^6$ specifically represents an ethylene, a propylene, a butylene, a hexylene, an octylene, and a cyclohexylene, and so on, and $R^7$ represents an alkyl group having 1 to 30 carbon atoms, specifically a methyl group, an ethyl group, a propyl group, a butyl group, a pentyl group, a hexyl group, a heptyl group, an octyl group, a stearyl group, and a bephenyl group.

$R^5$ preferably represents an alkyl group having 3 to 30 carbon atoms, and more preferably an alkyl group having carbon atoms 4 to 22.

Specific example of the specific isocyanate group-containing organic compound represented by the above general formula (2) includes the following ones.

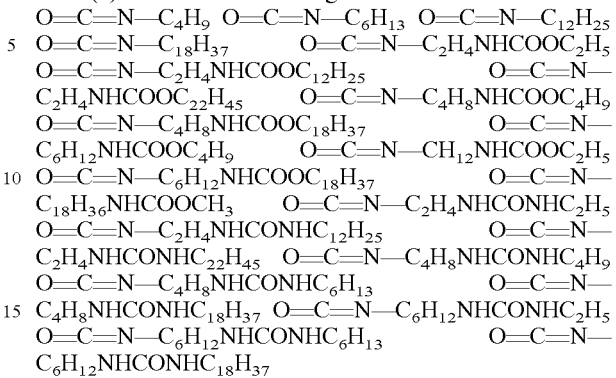

A method for producing a sugar compound to be blended into the cosmetic of the present invention is produced by urethane bond of the reaction of a hydroxyl group of a sugar compound, an isocyanate group-containing organopolysiloxane represented by the above general formula (1), and an isocyanate group-containing organic compound represented by the above general formula (2) (an organic compound having a group selected from an aliphatic hydrocarbon chain, an aromatic hydrocarbon chain, or a carbamoyl- or urea-bonded aliphatic hydrocarbon chain). In this reaction, a solvent is preferably used in view of reaction efficiency improvement and reaction control. Illustrative example of the solvent used in reaction includes an ester such as butyl acetate; a ketone such as methyl ethyl ketone and methyl isobutyl ketone, and cyclohexanone; an aromatic hydrocarbon such as toluene and xylene; an ether such as dibutyl ether, tetrahydrofuran, and dioxane; and an amide such as N,N-dimethylformamide and N-methylpyrrolidone, and these may be used alone or in combination with 2 or more other solvents.

The above reaction is carried out depending on the type of a solvent, normally 20 to 150° C. for 1 to 10 hours. A method for adding an isocyanate compound may be sequentially dropping, mixing dropping, or collectively adding, and known catalysts used in urethane bond, including an amine such as triethylamine, triethylenediamine, and N-methylmorpholine, an organic metal compound such as di-n-butyl tin dilaurate and stannous oleate, may be added. A desired sugar compound can be obtained by washing and drying after the reaction.

To obtain the sugar compound, the molar ratios of a saccharide, an isocyanate group-containing organopolysiloxane and an isocyanate group-containing organic compound are determined according to each amount introduced to a hydroxyl group per unit contained in the sugar compound. The isocyanate group-containing organopolysiloxane and the isocyanate group-containing organic compound, per mole of a hydroxyl group of the saccharide, are preferably in the range of 0.03 to 0.7. In fact, this reaction needs no reaction of all the hydroxyl groups with an isocyanate group-containing organopolysiloxane and an isocyanate group-containing organic compound, and part of a hydroxyl group may remain.

Since these ratios affect the solubility to each oil material, each ratio can be determined according to an oil material used. The sugar compound can be directly blended into a cosmetic, but its form is normally a solid having a film-forming property. Thus, it is preferably blended into a cosmetic, with being dissolved in an oil material or gelated in an oil material. The oil material can be similar to the one that can be blended into a later-mentioned cosmetic of the present invention.

A sugar compound containing a group selected from the organopolysiloxane of the present invention, an aliphatic hydrocarbon chain, an aromatic hydrocarbon chain, and a carbamoyl- or urea-bonded aliphatic hydrocarbon chain is suitable as an ingredient of all cosmetics for skins and hair for external use. The amount to be blended is preferably in the range of 0.05 to 40 parts by mass, relative to the total amount of the cosmetic.

Into the cosmetic of the present invention can be blended one, or two or more, of an oil material depending on its purpose. An oil material in any form of a solid, a semi-solid, and a liquid can be used provided that it is used in a usually used cosmetic.

Illustrative example of the natural vegetable and animal fatty oil and the semi-synthetic oil includes an avocado oil, a linseed oil, an almond oil, an insects wax, a perilla oil, an olive oil, a cacao butter, a kapok wax, a kaya oil, a carnauba wax, a liver oil, a candelilla wax, purified candelilla wax, a beef tallow, a neat's-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a rhea butter, a Chinese tung oil, a cinnamon oil, a jojoba wax, squalane, squalene, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse wax, a Persic oil, a palm oil, a palm kernel oil, a castor oil, a cured castor oil, a methyl ester of cured castor oil fatty acid, a sunflower oil, a grapeseed oil, a bayberry wax, a jojoba oil, a macadamia nut oil, a bees wax, a mink oil, a meadowfoam seed oil, a cotton seed oil, a cotton wax, a Japan wax, a Japan wax kernel oil, a montan wax, a coconut oil, a cured coconut oil, a tri-coconut oil fatty acid glyceride, a mutton tallow, a peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil.

Meanwhile, POE means polyoxyethylene (the same as below).

Illustrative example of the hydrocarbon oil includes a linear, a branched, and a volatile hydrocarbon oil; specifically such as an ozocerite, an α-olefin oligomer, a light isoparaffin, isododecane, isohexadecane, a light liquid isoparaffin, squalane, a synthetic squalane, a vegetable squalane, squalene, a ceresin, a paraffin, a paraffin wax, a polyethylene wax, a polyethylene/polypropylene wax, ethylene/propylene/styrene copolymer, butylene/propylene/styrene copolymer, a liquid paraffin, a liquid isoparaffin, a pristane, polyisobutylene, a hydrogenated isobutene, a microcrystalline wax, and Vaseline. Illustrative example of the higher fatty acids includes lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Illustrative example of the higher alcohol includes lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glyceryl ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropyl lauroylsarcosinate ester, and diisostearyl malate. Illustrative example of the glyceride oil includes acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

Illustrative example of the silicone oil includes a linear or a branched organopolysiloxane having low to high viscosity such as dimethyl polysiloxane, tristrimethylsiloxy methyl silane, caprylyl methicone, phenyl trimethicone, tetrakistrimethylsiloxy silane, methyl phenyl polysiloxane, methyl hexyl polysiloxane, methyl hydrogen polysiloxane, and dimethylsiloxane/methyl phenyl siloxane copolymer; a cyclic organopolysiloxane such as octamethyl ciclotetrasiloxane, decamethyl cyclopentasiloxane, dodecamethyl cyclohexasiloxane, tetramethyl tetrahydrogen ciclotetrasiloxane, and tetramethyl tetraphenyl ciclotetrasiloxane; a silicone rubber such as an amino-modified organopolysiloxane, a pyrrolidone-modified organopolysiloxane, a pyrrolidone carboxylate-modified organopolysiloxane, a dimethyl polysiloxane gum of a high degree of polymerization, an amino-modified organopolysiloxane gum, and a dimethylsiloxane/methyl phenyl siloxane copolymer gum; a solution of a silicone gum or rubber of a cyclic organopolysiloxane, trimethylsiloxy silicic acid, a cyclic siloxane solution of trimethylsiloxy silicic acid, a silicone modified with a higher alkoxy such as stearoxysilicone, a higher fatty acid-modified silicone, an alkyl-modified silicone, a long chain alkyl-modified silicone, an amino-modified silicone, a fluorine-modified silicone, and a solution containing a dissolved silicone resin. Illustrative example of the fluorine oil material includes perfluoro polyether, perfluoro decalin, and perfluoro octane.

Amount of these oil materials to be blended is dependent on the form of the cosmetic; but it is preferably in the range of 1 to 98% by mass, relative to the total amount of the cosmetic.

The cosmetic of the present invention may be blended with water depending on the purpose thereof. Amount of water to be blended is dependent on the form of the cosmetic; but it is preferably in the range of 1 to 95% by mass, relative to the total amount of the cosmetic.

The cosmetic of the present invention may use, depending on the purpose thereof, one, or two or more kinds of a compound having an alcoholic hydroxyl group in a molecular structure.

Illustrative example of the compound having an alcoholic hydroxyl group that can be added in the present invention includes a lower alcohol such as ethanol and isopropanol; a sugar alcohol such as sorbitol and maltose; a sterol such as cholesterol, sitosterol, phytosterol, and lanosterol; and a polyhydric alcohol such as butylene glycol, propylene glycol, dibutylene glycol, and pentylene glycol. Amount thereof to be blended is preferably in the range of 0.1 to 98% by mass, relative to the total amount of the cosmetic.

The cosmetic of the present invention may use, depending on the purpose thereof, a water-soluble or a water-swelling polymer.

Illustrative example thereof includes a plant polymer such as an Arabia gum, tragacanth, galactan, a carob gum, a guar gum, a karaya gum, carrageenan, pectin, agar, quince seed (marmelo), starch (rice, corn, potato, wheat, and so on), an algae colloid, a trant gum, a locust bean gum; a microbial polymer such as a xanthan gum, dextran, succinoglucan, and pullulan; an animal polymer such as collagen, casein, albumin, and gelatin; a starch polymer such as carboxymethyl starch and methyl hydroxypropyl starch; a cellulose polymer such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose; an alginic acid polymer such as sodium alginate and propylene glycol alginate ester; a vinyl polymer such as polyvinyl methyl ether and carboxy vinyl polymer; a polyoxyethylene polymer; a polyoxyethylene polyoxypropylene copolymer; an acryl polymer such as sodium polyacrylate, polyethyl acrylate, polyacrylamide, and an acryloyldimethyl taurate salt copolymer; other synthetic water-soluble polymer such as polyethyleneimine and a cationic polymer; and an inorganic water-soluble polymer such as bentonite, aluminum magnesium silicate, montmorillonite, beidellite, nontronite, saponite, hectorite, and anhydrous silicic acid. Examples of these water-soluble polymers include a film-forming agent such as a polyvinyl alcohol and a polyvinyl pyrrolidone. Amount of these polymers to be blended is preferably in the range of 0.1 to 25% by mass, relative to the total amount of the cosmetic.

The cosmetic of the present invention may use, depending on the purpose thereof, one, or two or more kinds of powders and/or coloring agents. As to the powder like this, any powder may be used regardless of its form (spherical, needle-like, plate-like, and so on), its particle diameter (fumed, microparticle, pigment-class, and so on), and its particle structure (porous, non-porous, and so on), provided that the powder is used in a usual cosmetic. Illustrative example of the powder includes an inorganic powder, an organic powder, a surfactant metal salt powder, a color pigment, a pearl pigment, a metal powder pigment, a tar pigment, and a natural dye.

Specific example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montmorillonite, hectorite, zeolite, ceramics powder, dibasic calcium phosphate, alumina, aluminum hydroxide, boron nitride, and silica.

Specific example of the organic powder includes a polyamide powder, a polyester powder, a polyethylene powder, a polypropylene powder, a polystyrene powder, a polyurethane, a benzoguanamine powder, a polymethyl benzoguanamine powder, a tetrafluoroethylene powder, a polymethyl methacrylate powder, cellulose, a silk powder, a nylon powder, a 12 nylon powder, a 6 nylon powder, a silicone powder, styrene-acrylic acid copolymer, divinyl benzene-styrene copolymer, a vinyl resin, an urea resin, a phenolic resin, a fluorinated resin, a silicone resin, an acryl resin, a melamine resin, an epoxy resin, a polycarbonate resin, a fine crystalline fiber powder, a starch powder, and lauroyl lysine.

Specific example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Specific example of the color pigment includes an inorganic red pigment such as iron oxide, iron hydroxide, and iron titanate; an inorganic brown pigment such as γ-iron oxide; an inorganic yellow pigment such as a yellow iron oxide and a yellow earth; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders.

Specific example of the pearl pigment includes a mica coated with titanium oxide, titanium oxide-coated mica, oxychloro bismuth, oxychloro bismuth coated with titanium oxide, a talc coated with titanium oxide, fish scale foil, and a color mica coated with titanium oxide.

Specific example of the metal powder pigment includes an aluminum powder, a copper powder, and a stainless powder.

Specific example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

Specific example of the natural dye includes carminic acid, laccaic acid, carthamin, brazilin, and crocin.

In addition, usable are a powder obtained by hybridizing, or treating these powders, with a general oil material, a silicone oil, a fluorine-containing compound, a surfactant, and the like; a powder treated with a hydrolyzable silyl group or with an alkyl group having a hydrogen atom directly bonded to a silicon atom; an organopolysiloxane with any one of a linear type and a branched type or both, having a hydrolyzable silyl group or a hydrogen atom directly bonded to a silicon atom; an organopolysiloxane with any one of a linear type and a branched type or both, having a hydrolyzable silyl group or a hydrogen atom directly bonded to a silicon atom and co-modified with a long chain alkyl group; an organopolysiloxane with any one of a linear type and a branched type or both, having a hydrolyzable silyl group or a hydrogen atom directly bonded to a silicon atom and co-modified with a polyoxyalkylene group; an acryl-silicone copolymer having a hydrolyzable silyl group or a hydrogen atom directly bonded to a silicon atom; as appropriate, a mixture of one, or two or more of them.

Amount of the powder to be blended is preferably 0.1 to 99% by mass, relative to the total amount of the cosmetic. Especially in the case of a powdery solid cosmetic, the amount thereof is preferably 80 to 99% by mass, relative to the total amount of the cosmetic.

The cosmetic of the present invention may also use, depending on the purpose thereof, one, or two or more kinds of surfactants. As to the surfactants like this, there are an anionic, a cationic, a nonionic and an amphoteric surfactant;

and in the present invention, there is no particular restriction, and thus any of them may be used provided that the surfactant is used in a usual cosmetic.

Illustrative example of the anionic surfactant includes a fatty acid soap such as sodium stearate and triethanolamine palmitate, an alkyl ether carboxylic acid and a salt thereof, a salt of a condensation product between an amino acid and a fatty acid, an alkane sulfonate salt, an alkene sulfonate salt, a sulfonate salt of a fatty acid ester, a sulfonate salt of a fatty acid amide, a sulfonate salt of a formalin condensate, an alkyl sulfate ester salt, a sulfonate ester salt of a secondary alcohol, a sulfate ester salt of an alkyl and an allyl ether, a sulfate salt of a fatty acid ester, a sulfate salt of a fatty acid alkylolamide, a sulfate salt of a Turkey red oil and so on, an alkyl phosphate salt, an ether phosphate salt, an alkyl allyl ether phosphate salt, an amide phosphate salt, an N-acyl lactate salt, an N-acylsarcosinate salt, and an N-acylamino acid. Illustrative example of the cationic surfactant includes an alkyl amine salt, an amine salt such as between a fatty acid derivative and a polyamine or an aminoalcohol, an alkyl quaternary ammonium salt, an aromatic quaternary ammonium salt, a pyridinium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glucoside fatty acid ester, an alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesteryl ether, a linear or a branched polyoxyalkylene-modified organopolysiloxane, a linear or a branched organopolysiloxane co-modified with a polyoxyalkylene and an alkyl, a linear or a branched polyglycerin-modified organopolysiloxane, a linear or a branched organopolysiloxane co-modified with polyglycerin and an alkyl, an alkanol amide, a sugar ether, and a sugar amide. Illustrative example of the amphoteric surfactant includes a betaine, phosphatidylcholine, an aminocarboxylic acid salt, an imidazoline derivative, and an amido amine type.

Among these surfactants, a linear or a branched organopolysiloxane having a polyoxyalkylene chain or a polyglycerin chain in its molecular structure, or the linear or the branched organopolysiloxane further having a long chain alkyl group having 6 to 20 carbon atoms is preferable.

In these surfactants, amount of a hydrophilic polyoxyalkylene group or a polyglycerin group is preferably 10 to 70% by mass in its molecular structure; and in addition, amount thereof to be blended in a cosmetic is preferably 0.1 to 20% by mass, or particularly preferably 0.2 to 10% by mass, relative to the total amount of the cosmetic.

The cosmetic of the present invention may contain, depending on the purpose thereof, one, or two or more silicone resins.

The silicone resin is preferably an acryl silicone resin, i.e. a graft or a block copolymer of an acryl and a silicone. It is also possible to use an acryl silicone resin containing in its molecular structure at least one kind selected from the group consisting of a pyrrolidone moiety, a long chain alkyl moiety, a polyoxyalkylene moiety, a fluoroalkyl moiety, and an anion moiety such as a carboxylic acid.

The silicone resin is preferably a silicone net-work compound comprising a resin composed of an $R^{1s}_3SiO_{0.5}$ unit and an $SiO_2$ unit; a resin composed of an $R^{1s}_3SiO_{0.5}$ unit and an $R^{1s}_2SiO$ unit, and an $SiO_2$ unit; a resin composed of an $R^{1s}_3SiO_{0.5}$ unit and an $R^{1s}SiO_{1.5}$ unit; a resin composed of an $R^{1s}_3SiO_{0.5}$ unit, an $R^{1s}_2SiO$ unit, and an $R^{1s}SiO_{1.5}$ unit; and a resin composed of an $R^{1s}_3SiO_{0.5}$ unit, an $R^{1s}_2SiO$ unit, an $R^{1s}SiO_{1.5}$ unit, and an $SiO_2$ unit ($R^{1s}$ represents an organic group). It is also possible to use a net-work silicone compound containing in its molecular structure at least one kind selected from the group consisting of a pyrrolidone moiety, a long chain alkyl moiety, a polyoxyalkylene moiety, a fluoroalkyl moiety, and an amino moiety. When silicone resins such as an acrylic silicone resin and a net-work silicone compound are used, amount thereof to be blended into a cosmetic is preferably 0.1 to 20% by mass, or more preferably 1 to 10% by mass, relative to the total amount of the cosmetic.

The cosmetic of the present invention may also use, depending on the purpose thereof, one, or two or more kinds of a composition comprising crosslinking organopolysiloxane and an oil material that is a liquid at room temperature. It is preferable that this crosslinking organopolysiloxane swell by absorbing the liquid oil whose amount is more than own weight of the crosslinking organopolysiloxane. Here, the liquid oil such as the above-mentioned silicone oil, hydrocarbon oil, ester oil, natural vegetable and animal oil, semi-synthetic oil, and fluorine oil may be used; and illustrative example thereof includes low viscous silicone oil having viscosity of 0.65 to 100.0 mm$^2$/second (25° C.); a hydrocarbon oil such as a liquid paraffin, squalene, isododecane, and isohexadecane; a glyceride oil such as trioctanoin; an ester oil such as isotridecyl isononanoate, an N-acyl glutamate ester, and lauroyl ester sarcosinate; and a natural vegetable and animal oil such as a macadamia nut oil. It is preferable that the crosslinking agent of this crosslinking organopolysiloxane have two or more reactive vinyl moieties in its molecular structure and form a crosslinking structure by reacting with a hydrogen atom directly bonded to a silicon atom. Illustrative example of the crosslinking agent having two or more reactive vinyl moieties in its molecular structure includes an organopolysiloxane containing two or more vinyl groups in its molecular structure, a polyoxyalkylene containing two or more allyl groups in its molecular structure, a polyglycerin containing two or more allyl groups in its molecular structure, and an α,ω-alkenyl diene.

Further, a crosslinking organopolysiloxane containing in one molecular structure at least one kind selected from the group consisting of a polyoxyalkylene moiety, a polyglycerin moiety, a long chain alkyl moiety, an alkenyl moiety, an aryl moiety, and a fluoroalkyl moiety. Amount of the composition comprising the crosslinking organopolysiloxane and the oil material that is a liquid at room temperature is, if it is used, preferably 0.1 to 80% by mass, or more preferably 1 to 50% by mass, relative to the total amount of the cosmetic.

The cosmetic of the present invention may contain, depending on the purpose thereof, one, or two or more kinds of a silicone-modified olefin wax obtained by an addition reaction of an olefin wax, obtained by reacting an α-olefin and diene and containing an unsaturated group, with an organohydrogen polysiloxane containing one or more SiH bond in its molecular structure. As to the α-olefin, those having 2 to 12 carbon atoms such as ethylene, propylene, 1-butene, 1-hexene, and 4-methyl-1-pentene are preferable; and as to the diene, butadiene, isoprene, 1,4-hexadiene, vinyl norbornene, ethylidene norbornene, dicyclopentadiene, and so on are preferable. As to the organohydrogen polysiloxane containing the SiH bond, those having a linear structure, a siloxane branched structure, and so on may be used.

The cosmetic of the present invention may be added with a component generally used in a usual cosmetic; illustrative example thereof includes an oil-soluble gelation agent, a resin, an antiperspirant, a UV-absorber, a UV absorbing-scattering agent, a moisturizer, an antibacterial preservative, an antimicrobial agent, a fragrance, a salt, an antioxidant, a pH controller, a chelating agent, an algefacient, an anti-inflammatory agent, a skin care component (a skin-lightening agent, a cell activator, a rough skin-improver, a blood circulation promoter, a skin astringent agent, an antiseborrheic agent, and so on), a vitamin, an amino acid, a nucleic acid, a hormone, a clathrate compound, and a hair-immobilizing agent.

Illustrative example of the oil-soluble gelation agent is selected from the gelation agents including a metal soap such as aluminum stearate, magnesium stearate, and zinc myristate; an amino acid derivative such as N-lauroyl-L-glutamic acid and α,γ-di-n-butyl amine; a dextrin fatty acid ester such as dextrin palmitate ester, dextrin stearate ester, and dextrin 2-ethylhexoate palmitate ester; a sucrose fatty acid ester such as sucrose palmitate ester and sucrose stearate ester; a fructo-oligosaccharide fatty acid ester such as fructo-oligosaccharide stearate ester and fructo-oligosaccharide 2-ethylhexanoate ester; benzylidene derivative of sorbitol such as monobenzylidene sorbitol and dibenzylidene sorbitol; an organic-modified clay mineral such as dimethyl benzyl dodecyl ammonium montmorillonite clay and dimethyl dioctadecyl ammonium montmorillonite clay.

Illustrative example of the antiperspirant is selected from the antiperspirants including aluminum chlorohydrate, aluminum chloride, aluminum sesquichlorohydrate, zirconyl hydroxy chloride, aluminum zirconium hydroxy chloride, and aluminum zirconium glycine complex.

Illustrative example of the UV-absorber includes a benzoic acid UV-absorber such as para-amino benzoic acid; an anthranilic acid UV-absorber such as methyl anthranilate; a salicylic UV-absorber such as methyl salicylate, octyl salicylate, and trimethylcyclohexyl salicylate; a cinnamic acid UV-absorber such as octyl para-methoxy cinnamate; a benzophenone UV-absorber such as 2,4-dihydroxybenzophenone; a urocanic acid UV-absorber such as ethyl urocanate; a dibenzoylmethane UV-absorber such as 4-t-butyl-4'-methoxydibenzoylmethane; phenyl benzimidazole sulphonic acid; a triazine derivative. Illustrative example of the UV absorbing-scattering agent includes a particle, which absorbs and scatters a UV-beam, such as a titanium oxide microparticle, titanium oxide containing an iron microparticle, a zinc oxide microparticle, a cerium oxide microparticle, and a composite material thereof. A dispersed material obtained by dispersing the particle, which absorbs and scatters a UV-beam into an oil material prior to use may also be used.

Illustrative example of the moisturizer includes glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate salt, polyoxyethylene methyl glucoside, polyoxypropylene methyl glucoside, egg yolk lecithin, soybean lecithin, phosphatidyl choline, phosphatidyl ethanolamine, phosphatidyl serine, phosphatidyl glycerol, phosphatidyl inositol, and sphingo phospholipid.

Illustrative example of the antibacterial preservative includes para-oxybenzoate alkyl ester, benzoic acid, sodium benzoate, sorbic acid, potassium sorbate, and phenoxy ethanol. Illustrative example of the antibacterial agent includes benzoic acid, salicylic acid, carbolic acid, sorbic acid, a para-oxybenzoate alkyl ester, p-chloro-m-cresol, hexachlorophen, benzalkonium chloride, chlorhexidine chloride, trichlorocarbanilide, a photosensitive element, and phenoxy ethanol.

The fragrance is a natural fragrance or a synthetic fragrance. Illustrative example of the natural fragrance includes a plant fragrance extracted from a flower, a leaf, wood, pericarp, and so on; and an animal fragrance such as a musk and a civet. Illustrative example of the synthetic Fragrance includes hydrocarbons such as monoterpene; alcohols such as aliphatic alcohol and aromatic alcohol; aldehydes such as terpene aldehyde and aromatic aldehyde; ketones such as alicyclic ketone; esters such as terpene ester; lactones; phenols; oxides; nitrogen-containing compounds; and acetals, and so on.

As to the salt, an inorganic salt, an organic salt, an amine salt, and an amino acid salt may be mentioned. Illustrative example of the inorganic salt includes a sodium, a potassium, a magnesium, a calcium, an aluminum, a zirconium, and a zinc salt of an inorganic acid such as hydrochloric acid, sulfuric acid, carbonic acid, and nitric acid. Illustrative example of the organic salt includes a salt of an organic acid such as an acetic acid, dehydroacetic acid, citric acid, malic acid, succinic acid, ascorbic acid, and stearic acid. Illustrative example of the amine salt and amino acid salt includes a salt of an amine such as triethanol amine and an amino acid salt such as a glutamate salt. In addition, a salt of hyaluronic acid and chondroitin sulfate, an aluminum zirconium glycine complex, and a neutralized salt obtained by neutralization of an acid and a base used in a cosmetic prescription may be used.

Illustrative example of the antioxidant includes tocopherol, p-t-butylphenol, butyl hydroxy anisole, dibutyl hydroxy toluene, and phytin. Illustrative example of the pH controller includes lactic acid, citric acid, glycolic acid, succinic acid, tartaric acid, dl-malic acid, potassium carbonate, sodium bicarbonate, and ammonium bicarbonate. Illustrative example of the chelating agent includes alanine, sodium edetate, sodium polyphosphate, sodium metaphosphate, and phosphoric acid. Illustrative example of the algefacient includes L-menthol and camphor. Illustrative example of the anti-inflammatory agent includes allantoin, glycyrrhizinic acid and its salt, glycyrrhetic acid, stearyl glycyrrhetinate, tranexamic acid, and azulene.

Illustrative example of the skin care component includes a skin-lightening agent such as a placenta extract, arbutin, glutathione, and a saxifrage extract; a cell activator such as a royal jelly, a photosensitive element, a cholesterol derivative, and an extract from hemolysed blood of a young calf; a rough-skin improver; a blood circulation promoter such as nonylic acid warenylamide, benzyl niconinate ester, β-butoxyethyl niconinate ester, capsaicin, zingerone, cantharides tincture, ichthammol, caffeine, tannic acid, α-borneol, niconic acid tocopherol, inositol hexanicotinate, cyclandelate, cinnarizine, tolazoline, acetyl choline, verapamil, cepharanthine, and γ-orizanol; a skin astringent agent such as zinc oxide and tannic acid; and an antiseborrheic agent such as sulfur and thianthol.

Illustrative example of the vitamin includes a vitamin A such as a vitamin A oil, retinol, retinol acetate, and retinol palmitate; a vitamin B including vitamin B2 such as riboflavin, riboflavin butyrate, and a flavin adenine nucleotide, a vitamin B6 such as pyridoxine hydrochloride salt, pyridoxine dioctanoate, and pyridoxine tripalmitate, a vitamin B12 and its derivative, and vitamin B15 and its derivative; a vitamin C such as L-ascorbic acid, L-ascorbic acid dipalmitate ester, sodium L-ascorbic-2-sulfate, and dicalcium L-ascorbic acid phosphate diester; a vitamin D such as ergocalciferol and cholecalciferol; a vitamin E such as α-tocopherol, β-tocopherol, γ-tocopherol, dl-α-tocopherol acetate, dl-α-tocopherol nicotinate, and dl-α-tocopherol succinate; a vitamin H; a vitamin P; a nicotinic acid such as nicotinic acid, benzyl nicotinate, and a nicotinic acid amide; a pantothenic acid such as calcium pantothenate, D-pantothenyl alcohol, pantothenyl ethyl ether, and acetyl pantothenyl ethyl ether; and biotin.

Illustrative example of the amino acid includes glycine, valine, leucine, isoleucine, serine, threonine, phenylalanine, arginine, lysine, aspartic acid, glutamic acid, cystine, cysteine, methionine, and tryptophan. Illustrative example of the nucleic acid includes deoxyribonucleic acid. Illustrative example of the hormone includes estradiol and ethenyl estradiol.

Illustrative example of the clathrate compound includes cyclodextrin.

As to the hair-immobilizing polymer, an amphoteric polymer, an anionic polymer, a cationic polymer, and a nonionic polymer may be mentioned. Illustrative example of the hair-immobilizing polymer includes a polyvinyl pyrrolidone polymer such as polyvinyl pyrrolidone and vinyl pyrrolidone/vinyl acetate copolymer; an acidic vinyl ether polymer such as methyl vinyl ether/maleic anhydride alkyl half-ester copolymer; an acidic polyvinyl acetate polymer such as vinyl acetate/crotonic acid copolymer; an acidic acryl polymer compound such as a (meta)acrylic acid/alkyl(meta)acrylate copolymer and a (meta)acrylic acid/alkyl(meta)acrylate/alkyl acrylamide copolymer; and an amphoteric acryl polymer such as an N-methacryloylethyl-N,N-dimethyl ammonium/α-N-methylcarboxybetaine/alkyl(meta)acrylate copolymer and hydroxypropyl(meta)acrylate/butylaminoethyl methacrylate/acrylic acid octyl amide copolymer. In addition, a polymer derived from a nature such as cellulose or its derivative, and keratin and collagen or a derivative thereof may be used suitably.

In the present invention, the form or the configuration of the cosmetic is not particularly restricted; and thus, any of a water-base, an oil-base, a water-in-oil emulsion, an oil-in-water emulsion, a non-aqueous emulsion, a multi-emulsion such as W/O/W and O/W/O may be used.

Illustrative example of the cosmetic in the present invention includes a skin care cosmetic such as a beauty lotion, a milky lotion, a cream, a cleansing cream, a pack, an oil liquid, a massage material, a liquid cosmetic, a beauty oil, a cleansing lotion, a deodorant, a hand cream, a lip cream, and a wrinkle concealer; a make-up cosmetic such as a make-up foundation, a concealer, a white powder, a powder foundation, a liquid foundation, a cream foundation, an oil foundation, a rouge, an eye shadow, a mascara, an eye liner, an eye brow, and a lipstick; a hair cosmetic such as a shampoo, a rinse, a treatment, and a setting material; a UV-protective cosmetic such as antiperspirant, a sunscreen oil, a sunscreen lotion, and a sunscreen cream.

Particularly, a cosmetic containing water in the form of emulsion is suitable as a makeup foundation action, a facial liquid foundation, a sunscreen lotion and a sunscreen cream, and so on.

The cosmetic can be in the form of a liquid, an emulsion, a cream, a solid, a paste, a gel, a powder, a press, a multilayer, a mousse, a spray, a stick, a pencil, and so on.

If the cosmetic of the present invention includes a powder, the cosmetic is preferably in the form of a liquid, a paste, or a solid, with the powder being dispersed due to favorable handleability.

EXAMPLES

Hereinafter, the present invention will be described in more detail with reference to the following Examples and Comparative Examples; but the present invention is not limited thereto.

Synthesis Example 1

A pullulan (PF-20 product from Hayashibara Co., Ltd.) that was dried at 110° C. for 2 hours dry (5 g), an N-methylpyrrolidone (150 g) and a triethylamine (0.5 g) were dissolved by heating at 120° C. in a 500 ml reactor. Thereafter, an isocyanate group-containing organopolysiloxane (20 g) represented by the following general formula (4) and a stearylisocyanate (7.9 g) were charged thereinto, mixed and dropped.

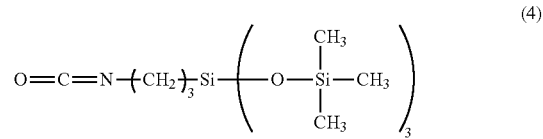

After the mixture was agitated at 120° C. for 3 hours for reaction, a reaction liquid was agitated and added to water (500 g), the resulting deposit was filtered off, and washed with water (500 g) and methanol each twice to be dried to obtain a white solid (24.3 g) (yield: 73.9%). After the white solid was subjected to $^1$H-NMR measurement of a molar ratio obtained by substituting with a hydroxyl group, an R ratio of a sugar unit represented by the following formula (5) (hydrogen/organopolysiloxane moiety/stearyl moiety) was 0.40/0.35/0.25.

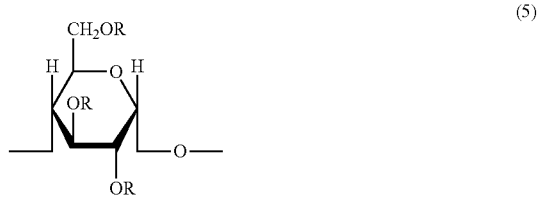

Synthesis Example 2

A pullulan (PF-20 product from Hayashibara Co., Ltd.) that was dried at 110° C. for 2 hours dry (5 g), an N-methylpyrrolidone (150 g) and a di-n-butyl tin dilaurate (0.5 g) were dissolved by heating at 120° C. in a 500 ml reactor. The isocyanate group-containing organopolysiloxane represented by the above general formula (4) (20 g) and a substance represented by the following formula (6) (9.6 g) were charged thereinto, mixed and dropped.

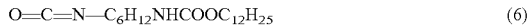

$$O=C=N-C_6H_{12}NHCOOC_{12}H_{25} \qquad (6)$$

After the mixture was agitated at 120° C. for 3 hours for reaction, a reaction liquid was agitated and added in water (500 g), filtered off a resulting deposit, and washed with water (500 g) and methanol each twice to be dried to obtain a white solid (24.3 g) (yield: 70.1%). After the white solid was subjected to $^1$H-NMR measurement of a molar ratio obtained by substituting with a hydroxyl group, an R ratio of a sugar unit represented by the following formula (5) (hydrogen/organopolysiloxane moiety/$C_6H_{12}NHCOOC_{12}H_{25}$ moiety) was 0.41/0.37/0.22.

Synthesis Example 3

A hydroxypropyl cellulose (LH-21 product from Shin-Etsu Chemical Co., Ltd., a hydroxypropoxy group: 11%) that was dried at 110° C. for 2 hours (5 g), an N-methylpyrrolidone (150 g) and a triethylamine (0.5 g) were heated and dispersed at 120° C. in a 500 ml reactor. The isocyanate group-containing organopolysiloxane represented by the above general formula (4) (18 g) and a stearylisocyanate (7.0 g) were charged therein, mixed and dropped. After the mixture was agitated at 120° C. for 3 hours for reaction, a reaction liquid was agitated and added in water (500 g), a resulting deposit was filtered off, washed with water (500 g) and methanol each twice to be dried to obtain a white solid (19.3 g) (yield: 64.3%). After the white solid was subjected to $^1$H-NMR measurement of a molar ratio obtained by substituting with a hydroxyl group, an R ratio of a sugar unit represented by the following formula (5) (hydrogen/organopolysiloxane moiety/stearyl moiety) was 0.55/0.28/0.17.

Synthesis Example 4

The compound of the Synthesis Example 1 and a decamethyl cyclopentasiloxane were charged into a nitrogen-substituted separable flask and dissolved uniformly with a glass stirrer at 80° C. to prepare a 10% by mass solution.

Synthesis Example 5

The compound of the Synthesis Example 1 and a diphenylsiloxyphenyl trimethicone were charged into a nitrogen-substituted separable flask and dissolved uniformly with a glass stirrer at 80° C. to prepare a 20% by mass solution.

Synthesis Example 6

The compound of the Synthesis Example 2 and an isododecane were charged into a nitrogen-substituted separable flask and dissolved uniformly with a glass stirrer at 80° C. to prepare a 10% by mass solution.

Synthesis Example 7

The compound of the Synthesis Example 3 and a diphenylsiloxyphenyl trimethicone were charged into a nitrogen-substituted separable flask and dissolved uniformly with a glass stirrer at 80° C. to prepare a 20% by mass solution.

Examples 1 and 2 and Comparative Example 1

A milky cream foundation of compositions as shown in Table 1 was prepared.

TABLE 1

| No. | Composition (% by mass) | Example 1 | Example 2 | Comparative Example 1 |
|---|---|---|---|---|
| 1 | Crosslinking polyether-modified silicone (note 1) | 5.0 | 5.0 | 5.0 |
| 2 | Crosslinking dimethylpolysiloxane (note 2) | 6.0 | 6.0 | 6.0 |
| 3 | Polyether-modified silicone (note 3) | 1.0 | 1.0 | 1.0 |
| 4 | Dimethylpolysiloxane (note 4) | 2.0 | 2.0 | 2.0 |
| 5 | Decamethylcyclopentasiloxane | 5.3 | 5.3 | 5.3 |
| 6 | Triethylhexanoin | 4.0 | 4.0 | 4.0 |
| 7 | Neopentyl glycol dioctanoate | 2.0 | 2.0 | 2.0 |
| 8 | Polymethylsilsesquioxane powder (note 5) | 1.5 | 1.5 | 1.5 |
| 9 | 1,3-BG | 5.0 | 5.0 | 5.0 |
| 10 | Sodium chloride | 0.5 | 0.5 | 0.5 |
| 11 | Water | 50.0 | 50.0 | 50.0 |
| 12 | Silicone-treated titanium oxide (note 6) | 8.65 | 8.65 | 8.65 |
| 13 | Silicone-treated red iron oxide (note 6) | 0.45 | 0.45 | 0.45 |
| 14 | Silicone-treated yellow iron oxide (note 6) | 0.75 | 0.75 | 0.75 |
| 15 | Silicone-treated black iron oxide (note 6) | 0.15 | 0.15 | 0.15 |
| 16 | Dissolved product of Synthesis Example 4 | 6.0 | — | — |
| 17 | Dissolved product of Synthesis Example 6 | — | 6.0 | — |
| 18 | Siliconized pullulan solution (note 7) | — | — | 6.0 |
| 19 | Antioxidant | 0.5 | 0.5 | 0.5 |
| 20 | Preservative | 1.0 | 1.0 | 1.0 |
| 21 | Fragrance | 0.2 | 0.2 | 0.2 |
|  | Total | 100 | 100 | 100 |

(note 1): Product from Shin-Etsu Chemical Co., Ltd.; KSG-210
(note 2): Product from Shin-Etsu Chemical Co., Ltd.; KSG-15
(note 3): Product from Shin-Etsu Chemical Co., Ltd.; KF-6017
(note 4): Product from Shin-Etsu Chemical Co., Ltd.; KF-96A-6cs
(note 5): Product from Shin-Etsu Chemical Co., Ltd.; KMP-590
(note 6): Product from Shin-Etsu Chemical Co., Ltd.; KF-9909-treated
(note 7): The siliconized pullulan (Japanese Examined Patent Publication No. H10-29910) whose R ratio (a molar ratio obtained by substituting with a hydroxyl group) of a pullulan and an isocyanate group-containing organopolysiloxane represented by the general formula (4) is 0.52/0.48, and a decamethyl cyclopentasiloxane were charged into a nitrogen-substituted separable flask and dissolved uniformly with a glass stirrer at 80° C. to prepare a 10% by mass solution.

[Preparation of Cosmetic]

Components (1) to (4), part of component (5), components (6) to (8), components (16) to (19) and component (20) mixed uniformly with agitation. Components (9) and (10) that were dissolved uniformly in component (11) were gradually added thereinto for emulsification. Components (12) to (15) and a remainder of component (5), and component (21) were added thereto and mixed. The emulsion was filled in a specific container to prepare a milky cream foundation. The milky cream foundation thus obtained was evaluated below.

[Evaluation of Usability]

As to the milky cream foundation obtained, 50 female special panelists were asked to evaluate spreadability on application, stickiness, irregular color tone of finishing and cosmetic sustainability (evaluated 8 hours after application) according to the following criteria to obtain average scores.

[Secondary Adhesion-Preventing Effect]

The milky cream foundation was applied on the forehead of the special panelists in a similar manner. 20 minutes after application, a tissue paper was placed on the specialist's forehead to evaluate secondary adhesion-preventing effect of the cosmetic according to the following criteria. The scores were averaged.

TABLE 2

| Score | Spreadability | Stickiness | Irregular color tone | Cosmetic sustainability | Secondary adhesion |
|---|---|---|---|---|---|
| 5 | Excellent | None | None | Excellent | None |
| 4 | Good | Almost none | Almost none | Good | Almost none |
| 3 | Fair | Fair | Fair | Fair | Fair |
| 2 | Poor | Slightly | Slightly | Poor | Slightly |
| 1 | Bad | Very much | Very much | Bad | Very much |

Table 3 shows the evaluation based on the average scores.
Very good: Obtained average score of 4.0 or more
Good: Obtained average score of 3.0 or more and less than 4.0
Fair: Obtained average score of 2.0 or more and less than 3.0
Bad: Obtained average score of less than 2.0

TABLE 3

|  | Example 1 | Example 2 | Comparative Example 1 |
|---|---|---|---|
| Spreadability | Very good | Good | Bad |
| Stickiness | Very good | Very good | Fair |
| Irregular color tone | Very good | Very good | Good |
| Cosmetic sustainability | Very good | Very good | Fair |
| Secondary adhesion | Very good | Very good | Fair |

As shown in Table 3, the cosmetic of the present invention is remarkably excellent not only in cosmetic sustainability and secondary adhesion prevention, but also in usability, compared with Comparative Example 1.

Examples 3 and 4 and Comparative Example 2

A lipstick of compositions as shown in Table 4 was prepared.

TABLE 4

| No. | Composition (% by mass) | Example 3 | Example 4 | Comparative Example 2 |
|---|---|---|---|---|
| 1 | Candelilla wax | 4.0 | 4.0 | 4.0 |
| 2 | Polyethylene | 2.0 | 2.0 | 2.0 |
| 3 | Microcrystalline wax | 3.0 | 3.0 | 3.0 |
| 4 | Ceresin | 7.0 | 7.0 | 7.0 |
| 5 | Stearyl-modified acrylic silicone resin (note 1) | 12.0 | 12.0 | 12.0 |
| 6 | Diphenyl dimethicone (note 2) | 17.8 | 17.8 | 17.8 |
| 7 | Dissolved product of Synthesis Example 5 | 8.0 | — | — |
| 8 | Dissolved product of Synthesis Example 7 | — | 8.0 | — |
| 9 | Siliconized pullulan solution (note 3) | — | — | 8.0 |
| 10 | Alkyl-modified branched polyglycerin-modified silicone (note 4) | 3.0 | 3.0 | 3.0 |
| 11 | macadamia nut oil | 15.0 | 15.0 | 15.0 |
| 12 | Hydrogenated polyisobutene | 8.0 | 8.0 | 8.0 |
| 13 | Isotridecyl isononanoate | 5.0 | 5.0 | 5.0 |
| 14 | Fragrance | 0.2 | 0.2 | 0.2 |

TABLE 4-continued

| No. | Composition (% by mass) | Example 3 | Example 4 | Comparative Example 2 |
|---|---|---|---|---|
| 15 | Lipstick pigment | 10 | 10 | 10 |
| 16 | Mica | 5 | 5 | 5 |
|  | Total | 100 | 100 | 100 |

(note 1): Product from Shin-Etsu Chemical Co., Ltd.; KP-561P
(note 2): Product from Shin-Etsu Chemical Co., Ltd.; KF-54
(note 3): A siliconized pullulan (Japanese Examined Patent Publication No. H10-29910) whose R ratio (a molar ratio obtained by substituting with a hydroxyl group) of a pullulan and an isocyanate group-containing organopolysiloxane represented by the general formula (4) is 0.52/0.48, and a decamethyl cyclopentasiloxane were charged into a nitrogen-substituted separable flask and dissolved uniformly with a glass stirrer at 80° C. to prepare a 20% by mass solution.
(note 4): Product from Shin-Etsu Chemical Co., Ltd.; KF-6105

<Preparation of Cosmetic>
A: Components 1 to 12 and components 15 and 16 were mixed uniformly by heating.
B: Components 13 and 14 were added thereto by heating and mixed uniformly; and then the mixture was filled in a specific airtight container to obtain a lipstick.

[Evaluation of Usability]
As to the lipstick obtained, 50 female special panelists were asked to evaluate spreadability, stickiness, irregular color tone of finishing, and cosmetic sustainability (evaluated 8 hours after application) like the above Example to obtain the average scores.

TABLE 5

|  | Example 3 | Example 4 | Comparative Example 2 |
|---|---|---|---|
| Spreadability | Very good | Good | Fair |
| Stickiness | Very good | Very good | Good |
| Irregular color tone | Very good | Very good | Fair |
| Cosmetic sustainability | Very good | Very good | Fair |

As shown in Table 5, the lipstick obtained exhibits neither stickiness nor greasiness nor blur, but favorable cosmetic sustainability was confirmed.

Examples of cosmetic Prescription will be described. Hereinafter, "spreadability" and "cosmetic sustainability" are evaluated according to the above criteria. As to the foundation, secondary adhesion prevention was also evaluated according to the above criteria.

Example 5

Powder Foundation

| (Components) | mass (%) |
|---|---|
| 1. Silicone-treated titanium oxide (note 1) | 12.0 |
| 2. Silicone-treated sericite (note 1) | 35.0 |
| 3. Lecithin-treated talc | 35.1 |
| 4. Lecithin-treated spherical shapenylon powder | 5.0 |
| 5. Silicone-treated colcothar (note 1) | 0.4 |
| 6. Silicone-treated yellow iron oxide(note 1) | 2.0 |
| 7. Silicone-treated ambergris (note 1) | 0.4 |
| 8. Silicone-treated black iron oxide (note 1) | 0.1 |
| 9. Dissolved product of Synthesis Example 4 | 3.0 |
| 10. Crosslinking dimethyl polysiloxane (note 2) | 4.0 |

| (Components) | mass (%) |
|---|---|
| 11. Glyceryl trioctanoate | 1.5 |
| 12. Silicone wax (note 3) | 1.5 |
| Total | 100.0 |

(note 1): Product from Shin-Etsu Chemical Co., Ltd.; KF-9909-treated
(note 2): Product from Shin-Etsu Chemical Co., Ltd.; KSG-16
(note 3): Product from Shin-Etsu Chemical Co., Ltd.; KP-562P <Preparation of Cosmetic>
A: Components 1 to 8 were mixed; and pulverized uniformly.
B: Components 9 to 12 were mixed uniformly.
C: Product B was added to product A to be mixed uniformly, and press-molded into mold to obtain a powder foundation.

The powder foundation obtained exhibited smooth spreadability, favorable cosmetic sustainability, and no secondary adhesion.

Example 6

Powder Foundation

| Components | mass (%) |
|---|---|
| 1. Caprylylsilane-treated mica (note 1) | 40.0 |
| 2. Silicone-treated talc (note 2) | 20.0 |
| 3. Silicone-treated titanium oxide (note 2) | 8.0 |
| 4. Silicone-treated microparticle titanium oxide (note 2) | 5.0 |
| 5. Silicone-treated-barium sulfate (note 2) | 8.9 |
| 6. Silicone-treated foundation pigment (note 2) | 7.0 |
| 7. Phenyl-modified hybrid silicone composite powder (note 3) | 2.0 |
| 8. Polymethylsilsesquioxane powder (note 4) | 0.4 |
| 9. Preservative | 0.5 |
| 10. Fragrance | 0.2 |
| 11. Dissolved product of Synthesis Example 5 | 3.0 |
| 12. Glyceryl trioctanoate | 3.0 |
| 13. Squalene | 1.0 |
| 14. Vaseline | 1.0 |
| Total | 100.0 |

(note 1): Product from Shin-Etsu Chemical Co., Ltd.; AES-3083-treated
(note 2): Product from Shin-Etsu Chemical Co., Ltd.; KF-9909-treated
(note 3): Product from Shin-Etsu Chemical Co., Ltd.; KSP-300
(note 4): Product from Shin-Etsu Chemical Co., Ltd.; KMP-590

<Preparation of Cosmetic>
A: Components 1 to 9 were mixed; and pulverized uniformly.
B: Components 11 to 14 were mixed uniformly; and the mixture was added to product A to be mixed uniformly.
C: Component 10 was added to product B; and press-molded in a mold to obtain a powder foundation.

The powder foundation obtained exhibited smooth spreadability, favorable cosmetic sustainability, and no secondary adhesion.

Example 7

Stick W/O Foundation

| Components | mass (%) |
|---|---|
| 1. Ceresin | 5.5 |
| 2. Stearoyl inulin | 2.0 |
| 3. Neopentyl glycol dioctanoate | 7.0 |
| 4. Triethylhexanoin | 4.0 |
| 5. Dimethyl polysiloxane (6cs) | 6.3 |
| 6. Dissolved product of Synthesis Example 7 | 3.0 |
| 7. Crosslinking polyglycerin-modified silicone (note 1) | 4.0 |
| 8. Alkyl-modified branched polyglycerin-modified silicone (note 2) | 1.5 |
| 9. Polymethylsilsesquioxane powder (note 3) | 1.0 |
| 10. Silicone-treated titanium oxide (note 4) | 9.0 |
| 11. Silicone-treated foundation pigment (note 5) | 5.0 |
| 12. Lecithin | 0.2 |
| 13. Polysorbate 80 | 0.3 |
| 14. 1,3-BG | 4.0 |
| 15. Preservative | 0.5 |
| 16. Fragrance | 0.2 |
| 17. Purified water | 46.5 |
| Total | 100.0 |

(note 1): Product from Shin-Etsu Chemical Co., Ltd.; KSG-710
(note 2): Product from Shin-Etsu Chemical Co., Ltd.; KF-6105
(note 3): Product from Shin-Etsu Chemical Co., Ltd.; KMP-590
(note 4): Product from Shin-Etsu Chemical Co., Ltd.; KF-9909-treated
(note 5): Product from Shin-Etsu Chemical Co., Ltd.; KF-9909-treated <Preparation of Cosmetic>
A: Components 1 to 9 were dissolved by heating; and mixed uniformly.
B: Components 10 to 13 and part of 14 were mixed; and the resulting mixture was dispersed with a roller.
C: A remainder of component 14, and components 15 and 17 were dissolved uniformly; and the resulting mixture was added to product B and dispersed uniformly by heating.
D: With agitation by heating, product C was added to product A; and component 16 was added thereto and filled in an airtight specific container to obtain a stick W/O foundation.

The stick W/O foundation obtained exhibited smooth spreadability, favorable cosmetic sustainability and no secondary adhesion.

Example 8

Solid Water-in-Oil Polyhydric Alcohol Milky Rouge

| (Components) | mass (%) |
|---|---|
| 1. Crosslinking polyglycerin-modified silicone (note 1) | 5.0 |
| 2. Crosslinking dimethyl polysiloxane (note 2) | 5.0 |
| 3. Decamethyl cyclopentasiloxane | 3.0 |
| 4. Dimethyl polysiloxane (6cs) | 19.7 |
| 5. Cetyl isooctanoate | 5.0 |
| 6. Dissolved product of Synthesis Example 7 | 10.0 |
| 7. Behenyl-modified acrylic silicone resin (note 3) | 3.0 |
| 8. Paraffin wax (melting point: 80° C.) | 9.0 |
| 9. Dimethyldistearyl ammonium hectorite | 0.3 |
| 10. Acrylic silicone-treated powder (note 4) | 25.0 |
| 11. Preservative | 0.5 |
| 12. Fragrance | 0.2 |
| 13. 1,3-butylene glycol | 14.3 |
| Total | 100.0 |

(note 1): Product from Shin-Etsu Chemical Co., Ltd.; KSG-710
(note 2): Product from Shin-Etsu Chemical Co., Ltd.; KSG-15
(note 3): Product from Shin-Etsu Chemical Co., Ltd.; KP-562P
(note 4): Product from Shin-Etsu Chemical Co., Ltd.; KP-574-treated <Preparation of Cosmetic>
A: Components 1 to 9 and component 12 were heated at 80° C.; and mixed uniformly.
B: Component 10 was added thereto; and dispersed uniformly.

C: Components 11 and 13 were mixed; and added to product B for emulsification after heating at 80° C., cast in a metallic dish, and then, after cooling, to obtain a solid water-in-oil polyhydric alcohol milky rouge.

The solid water-in-oil polyhydric alcohol milky rouge thus obtained exhibited smooth spreadability, and neither stickiness nor greasiness.

Example 9

Cream Lipstick

| (Components) | mass (%) |
|---|---|
| 1. Palmitic acid/dextrin ethylhexanoate (note 1) | 9.0 |
| 2. Triethylhexanoin | 7.0 |
| 3. Dissolved product of Synthesis Example 5 | 8.0 |
| 4. Alkyl-modified Crosslinking dimethyl polysiloxane (note 2) | 8.0 |
| 5. Alkyl-modified branched polyglycerin-modified silicone (note 3) | 2.0 |
| 6. Decamethyl cyclopentasiloxane | 35.0 |
| 7. 1,3-butylene glycol | 4.8 |
| 8. Purified water | 18.0 |
| 9. Coloring pigment | 6.0 |
| 10. Mica | 2.0 |
| 11. Fragrance | 0.2 |
| Total | 100.0 |

(note 1): Product from Chiba Flour Milling Co., Ltd.; leopard TT
(note 2): Product from Shin-Etsu Chemical Co., Ltd.; KSG-43
(note 3): Product from Shin-Etsu Chemical Co., Ltd.; KF-6105

<Preparation of Cosmetic>

A: Part of components 1 and 2 and components 3 to 6 were mixed uniformly by heating.

B: Component 9 was mixed with a remainder of component 2, dispersed with a roller; and added to product A to be mixed uniformly.

C: Components 7 and 8 were mixed, heated and added to product B for emulsification.

D: Components 10 and 11 were added to product C to obtain a cream lipstick.

The cream lipstick thus obtained exhibited smooth spreadability on the lip, and neither stickiness nor greasiness, but favorable cosmetic sustainability.

Example 10

Eye Liner

| (Components) | mass (%) |
|---|---|
| 1. Methyltrimethicone (note 1) | 20.0 |
| 2. Polyether-modified silicone (note 2) | 3.0 |
| 3. Dissolved product of Synthesis Example 5 | 33.5 |
| 4. Silicone net-work resin dissolved product (note 3) | 15.0 |
| 5. Dimethyldistearyl ammonium hectorite | 3.0 |
| 6. Silicone-treated black iron oxide (note 4) | 10.0 |
| 7. 1,3-butylene glycol | 4.5 |
| 8. Sodium sulfate | 0.5 |
| 9. Preservative | 0.5 |
| 10. Purified water | 10.0 |
| Total | 100.0 |

(note 1): Product from Shin-Etsu Chemical Co., Ltd.; TMF-1.5
(note 2): Product from Shin-Etsu Chemical Co., Ltd.; KF-6017
(note 3): Product from Shin-Etsu Chemical Co., Ltd.; KF-7312T
(note 4): Product from Shin-Etsu Chemical Co., Ltd.; KF-9901-treated <Preparation of Cosmetic>

A: Components 1 to 5 were mixed; and component 6 was added thereinto, and mixed uniformly and dispersed.

B: Components 7 to 10 were mixed.

C: Product B was added to product A for emulsification to obtain an eye liner.

The eye liner thus obtained exhibited smooth spreadability on eye lines, refreshing use feeling, and excellent cosmetic sustainability.

The volatile oil, part of this eye liner's prescription, is M3T, but can be replaced with an isododecane solution.

Example 11

Mascara

| (Components) | mass (%) |
|---|---|
| 1. Dissolved product of Synthesis Example 5 | 26.5 |
| 2. Palmitic acid/dextrin ethylhexanoate (note 1) | 3.0 |
| 3. Ceresin | 2.5 |
| 4. Behenyl-modified acrylic silicone resin (note 2) | 2.0 |
| 5. Bees wax | 3.5 |
| 6. Triethylhexanoin | 3.0 |
| 7. Dimethyldistearyl ammonium hectorite | 4.0 |
| 8. Lecithin | 0.5 |
| 9. Isododecane | 34.0 |
| 10. Silicone-treated pigment (note 3) | 5.0 |
| 11. Silica | 3.0 |
| 12. Talc | 12.0 |
| 13. Branched polyether-modified silicone (note 4) | 1.0 |
| Total | 100.0 |

(note 1): Product from Chiba Flour Milling Co., Ltd.; leopard TT
(note 2): Product from Shin-Etsu Chemical Co., Ltd.; KP-562P
(note 3): Product from Shin-Etsu Chemical Co., Ltd.; KF-9909-treated
(note 4): Product from Shin-Etsu Chemical Co., Ltd.; KF-6028P <Preparation of Cosmetic>

A: Components 7 and 13 were added to component 9; and, mixed uniformly by heating.

B: Components 1 to 6 and component 8 were added to product A; and mixed uniformly.

C: Components 10, 11 and 12 were added to product B; and mixed uniformly with a roller to obtain a mascara.

The mascara thus obtained exhibited smooth spreadability, easy attachment to eyelashes, non-stickiness, and excellent cosmetic sustainability.

Example 12

Cream Eye Shadow

| (Components) | mass (%) |
| --- | --- |
| 1. Decamethyl cyclopentasiloxane | 15.0 |
| 2. Dimethyl polysiloxane (6cs) | 4.0 |
| 3. Dissolved product of Synthesis Example 4 | 5.0 |
| 4. Branched polyether-modified silicone (note 1) | 1.5 |
| 5. Acrylic silicone resin-treated pigment (note 2) | 16.0 |
| 6. Sodium chloride | 2.0 |
| 7. Propylene glycol | 7.5 |
| 8. Preservative | 0.5 |
| 9. Purified water | 48.5 |
| Total | 100.0 |

(note 1): Product from Shin-Etsu Chemical Co., Ltd.; KF-6028P
(note 2): Product from Shin-Etsu Chemical Co., Ltd.; KP-574-treated <Preparation of Cosmetic>
A: Components 1 to 4 were mixed; and component 5 was added thereinto, mixed uniformly, and dispersed.
B: Components 6 to 9 were mixed.
C: Product B was added to product A for emulsification to obtain a cream eye shadow.

The cream eye shadow thus obtained exhibited smooth spreadability, neither greasiness nor powdery impression, but favorable cosmetic sustainability.

Example 13

Cream Eye Shadow

| (Components) | mass (%) |
| --- | --- |
| 1. Acrylic silicone resin dissolved product (note 1) | 3.0 |
| 2. Stearyl-modified acrylic silicone resin (note 2) | 2.0 |
| 3. Branched polyether-modified silicone (note 3) | 1.5 |
| 4. Decamethyl cyclopentasiloxane | 20.3 |
| 5. Dissolved product of Synthesis Example 4 | 10.0 |
| 6. Dimethyldistearyl ammonium hectorite | 1.2 |
| 7. Acrylic silicone resin-treated pigment (note 4) | 20.0 |
| 8. Spherical shapenylon | 3.0 |
| 9. Talc | 4.0 |
| 10. Ethanol | 5.0 |
| 11. Purified water | 30.0 |
| Total | 100.0 |

(note 1): Product from Shin-Etsu Chemical Co., Ltd.; KP-545
(note 2): Product from Shin-Etsu Chemical Co., Ltd.; KP-561P
(note 3): Product from Shin-Etsu Chemical Co., Ltd.; KF-6028P
(note 4): Product from Shin-Etsu Chemical Co., Ltd.; KP-574-treated <Preparation of Cosmetic>
A: Components 1 to 6 were mixed; and components 7 to 9 were added thereinto, mixed uniformly and dispersed.
B: Components 10 to 11 were mixed.
C: Product B was added to product A for emulsification to obtain a cream eye shadow.

The cream eye shadow thus obtained exhibited smooth spreadability, neither greasiness nor powdery impression, but excellent refreshing use feeling and favorable cosmetic sustainability.

Example 14

Sun-Cut Milky Lotion

| (Components) | mass (%) |
| --- | --- |
| 1. Crosslinking polyether-modified silicone (note 1) | 3.0 |
| 2. Crosslinking dimethyl polysiloxane (note 2) | 2.0 |
| 3. Branched polyether-modified silicone (note 3) | 1.0 |
| 4. Dissolved product of Synthesis Example 5 | 5.0 |
| 5. Decamethyl cyclopentasiloxane | 5.0 |
| 6. Isotridecyl isononanoate | 4.0 |
| 7. Titanium oxide dispersion (note 4) | 25.0 |
| 8. Zinc oxide dispersion (note 5) | 35.0 |
| 9. 1,3-Butylene glycol | 2.0 |
| 10. Sodium citrate | 0.2 |
| 11. Sodium chloride | 0.5 |
| 12. Purified water | 17.3 |
| Total | 100.0 |

(note 1): Product from Shin-Etsu Chemical Co., Ltd.; KSG-210
(note 2): Product from Shin-Etsu Chemical Co., Ltd.; KSG-15
(note 3): Product from Shin-Etsu Chemical Co., Ltd.; KF-6028P
(note 4): Product from Shin-Etsu Chemical Co., Ltd.; SPD-T5
(note 5): Product from Shin-Etsu Chemical Co., Ltd.; SPD-Z5

<Preparation of Cosmetic>
A: Components 1 to 6 were mixed uniformly.
B: Components 9 to 12 were mixed.
C: Product B was added to product A for emulsification; and components 7 and 8 were added thereinto to obtain a sun-cut milky lotion.

The sun-cut milky lotion thus obtained exhibited smooth spreadability, neither stickiness nor greasiness, but favorable perspiration resistance.

Example 15

Sun-Cut Cream

| (Components) | mass (%) |
| --- | --- |
| 1. Crosslinking polyether-modified silicone (note 1) | 3.0 |
| 2. Crosslinking dimethyl polysiloxane (note 2) | 2.0 |
| 3. Alkyl-modified branched polyether-modified silicone (note 3) | 1.0 |
| 4. Dissolved product of Synthesis Example 7 | 7.0 |
| 5. Decamethyl cyclopentasiloxane | 15.5 |
| 6. Octyl methoxycinnamate | 6.0 |
| 7. Acrylic silicone resin dissolved product (note 4) | 10.0 |
| 8. Lipophilized microparticle zinc oxide (note 5) | 20.0 |
| 9. 1,3-Butylene glycol | 1.8 |
| 10. Sodium citrate | 0.2 |
| 11. Sodium chloride | 0.5 |
| 12. Fragrance | 0.2 |
| 13. Purified water | 32.8 |
| Total | 100.0 |

(note 1): Product from Shin-Etsu Chemical Co., Ltd.; KSG-240
(note 2): Product from Shin-Etsu Chemical Co., Ltd.; KSG-15
(note 3): Product from Shin-Etsu Chemical Co., Ltd.; KF-6038
(note 4): Product from Shin-Etsu Chemical Co., Ltd.; KP-575
(note 5): Product from Shin-Etsu Chemical Co., Ltd.; AES-3083-treated <Preparation of Cosmetic>
A: Component 7 was added to part of component 5 to be mixed uniformly; and component 8 was added thereinto and dispersed with a bead mill.
B: Components 1 to 4 and a remainder of component 5, and component 6 were mixed uniformly.
C: Components 9 to 11 and component 13 were mixed uniformly.
D: Product C was added to product B for emulsification; and product A and component 12 were added thereinto to obtain a sun-cut cream.

The sun-cut cream thus obtained exhibited neither stickiness nor greasiness, but smooth spreadability and refreshing use feeling, and favorable cosmetic sustainability.

Example 16

Sun-Cut Lotion (Shaking Type)

| (Components) | mass (%) |
| --- | --- |
| 1. Branched polyether-modified silicone (note 1) | 2.0 |
| 2. Dissolved product of Synthesis Example 7 | 5.0 |
| 3. Dimethyl polysiloxane (6cs) | 3.0 |
| 4. Decamethyl cyclopentasiloxane | 7.8 |
| 5. Ethylhexyl methoxycinnamate | 7.5 |
| 6. Hybrid silicone composite powder (note 2) | 0.5 |
| 7. Dimethyldistearyl ammonium hectorite | 0.2 |
| 8. Zinc oxide dispersion (note 3) | 45.0 |
| 9. 1,3-butylene glycol | 3.0 |
| 10. Alcohol | 5.0 |
| 11. Sodium citrate | 0.2 |
| 12. Sodium chloride | 0.5 |
| 13. Purified water | 20.3 |
| Total | 100.0 |

(note 1): Product from Shin-Etsu Chemical Co., Ltd.; KF-6028P
(note 2): Product from Shin-Etsu Chemical Co., Ltd.; KSP-105
(note 3): Product from Shin-Etsu Chemical Co., Ltd.; SPD-Z6

<Preparation of Cosmetic>
A: Components 1 to 7 were mixed uniformly.
B: Components 9 to 13 were mixed.
C: Product B was added to product A for emulsification; and component 8 was added thereinto to obtain a shaking-type sun-cut lotion.

The sun-cut lotion thus obtained exhibited smooth spreadability, neither stickiness nor greasiness, but excellent cosmetic sustainability.

Example 17

Suntan Milky Lotion

| (Components) | mass (%) |
| --- | --- |
| 1. Crosslinking polyether-modified silicone (note 1) | 2.0 |
| 2. Crosslinking dimethyl polysiloxane (note 2) | 3.0 |
| 3. Polyether-modified silicone (note 3) | 1.5 |
| 4. Dissolved product of Synthesis Example 6 | 10.0 |
| 5. Dimethyl polysiloxane (6cs) | 10.0 |
| 6. Decamethyl cyclopentasiloxane | 15.3 |
| 7. Dihydroxyacetone | 2.0 |
| 8. Glycerin | 8.0 |
| 9. 1,3-butylene glycol | 5.0 |
| 10. Sodium citrate | 0.2 |
| 11. Sodium chloride | 0.5 |
| 12. Antioxidant | 0.5 |
| 13. Preservative | 0.5 |
| 14. Fragrance | 0.2 |
| 15. Purified water | 41.3 |
| Total | 100.0 |

(note 1): Product from Shin-Etsu Chemical Co., Ltd.; KSG-210
(note 2): Product from Shin-Etsu Chemical Co., Ltd.; KSG-15
(note 3): Product from Shin-Etsu Chemical Co., Ltd.; KF-6017

<Preparation of Cosmetic>
A: Components 1 to 6 were mixed uniformly.
B: Components 7 to 13 and component 15 were mixed.
C: Product B was added to product A for emulsification; and component 14 was added thereinto to obtain a suntan milky lotion.

The suntan milky lotion thus obtained exhibited neither stickiness nor greasiness, but smooth spreadability and refreshing use feeling.

Example 18

Suntan Cream

| (Components) | mass (%) |
| --- | --- |
| 1. Alkyl-modified Crosslinking polyether-modified silicone (note 1) | 4.0 |
| 2. Alkyl-modified Crosslinking dimethyl polysiloxane (note 2) | 2.0 |
| 3. Alkyl-modified branched polyether-modified silicone (note 3) | 1.0 |
| 4. Dissolved product of Synthesis Example 5 | 5.0 |
| 5. Decamethyl cyclopentasiloxane | 10.3 |
| 6. Stearyl-modified acrylic silicone (note 4) | 1.0 |
| 7. Dimethyl octyl para-aminobenzoic acid | 1.5 |
| 8. 4-t-butyl-4'-methoxy-dibenzoylmethane | 1.5 |
| 9. Kaolin | 0.5 |
| 10. Pigment | 8.0 |
| 11. Titanium oxide-coated mica | 8.0 |
| 12. Dioctadecyldimethyl ammonium chloride | 0.1 |
| 13. L-sodium glutamate | 3.0 |
| 14. 1,3-butylene glycol | 4.0 |
| 15. Sodium citrate | 0.2 |
| 16. Sodium chloride | 0.5 |
| 17. Antioxidant | 0.5 |
| 18. Preservative | 0.5 |
| 19. Fragrance | 0.2 |
| 20. Purified water | 48.2 |
| Total | 100.0 |

(note 1): Product from Shin-Etsu Chemical Co., Ltd.; KSG-320
(note 2): Product from Shin-Etsu Chemical Co., Ltd.; KSG-42
(note 3): Product from Shin-Etsu Chemical Co., Ltd.; KF-6038
(note 4): Product from Shin-Etsu Chemical Co., Ltd.; KP-561P <Preparation of Cosmetic>
A: Components 1 to 8 and components 17 and 18 were mixed by heating.
B: After component 12 and part of component 20 were heated with agitation, components 9 to 11 were added thereinto and dispersed.
C: Components 13 to 16 and a remainder of component 20 were uniformly dissolved, and mixed with product B.
D: With agitation, product C was gradually added to product A for emulsification, and then, after cooling, component 19 was added thereinto to obtain a suntan cream.

The suntan cream thus obtained exhibited fine texture, smooth spreadability, neither stickiness nor greasiness, but refreshing use feeling, and favorable cosmetic sustainability.

Example 19

Liquid W/O Foundation

| (Components) | mass (%) |
|---|---|
| 1. Decamethyl cyclopentasiloxane | 18.0 |
| 2. Dimethyl polysiloxane (6cs) | 2.0 |
| 3. Dissolved product of Synthesis Example 7 | 7.0 |
| 4. Alkyl-modified branched polyether-modified silicone (note 1) | 2.0 |
| 5. Paraethylhexyl methoxycinnamate | 3.0 |
| 6. Fluorine-modified silicone (note 2) | 2.0 |
| 7. Polymethylsilsesquioxane powder (note 3) | 1.5 |
| 8. Fluorine compound-treated foundation pigment (note 4) | 9.3 |
| 9. Fluorine compound-treated mica titanium (note 4) | 2.0 |
| 10. Silicone-treated microparticle titanium oxide (note 5) | 8.0 |
| 11. Alkyl-modified branched polyglycerin-modified silicone (note 6) | 1.2 |
| 12. Ethanol | 3.0 |
| 13. 1,3-butylene glycol | 4.3 |
| 14. Glycerin | 1.5 |
| 15. Magnesium sulfate | 0.5 |
| 16. Antioxidant | 0.5 |
| 17. Preservative | 0.5 |
| 18. Fragrance | 0.2 |
| 19. Purified water | 33.5 |
| Total | 100.0 |

(note 1): Product from Shin-Etsu Chemical Co., Ltd.; KF-6038
(note 2): Product from Shin-Etsu Chemical Co., Ltd.; FL-5
(note 3): Product from Shin-Etsu Chemical Co., Ltd.; KMP-590
(note 4): 5% coated with perfluoroalkylethyl diethanolamine phosfate
(note 5): Product from Shin-Etsu Chemical Co., Ltd.; KF-9909-treated
(note 6): Product from Shin-Etsu Chemical Co., Ltd.; KF-6105

<Preparation of Cosmetic>
A: Part of component 1 and Components 11 and 12 were mixed and uniformly dispersed.
B: Components 8 to 10 were mixed uniformly.
C: A remainder of component 1 and components 2 to 7 were mixed; and component B was added thereinto dispersed and mixed uniformly.
D: Components 13 to 18 were mixed uniformly.
E: With agitation, product D was gradually added to product C for emulsification; and product A and component 19 were added thereinto to obtain a liquid W/O foundation.

The liquid W/O foundation thus obtained exhibited neither stickiness nor greasiness, but smooth foam touch, smooth spreadability, favorable cosmetic sustainability, and no secondary adhesion.

Example 20

Hair Cream

| (Components) | mass (%) |
|---|---|
| 1. Decamethyl cyclopentasiloxane | 16.0 |
| 2. Methyl phenyl polysiloxane (note 1) | 2.0 |
| 3. Dissolved product of Synthesis Example 5 | 4.0 |
| 4. Squalene | 5.0 |
| 5. Silicone net-work resin dissolved product (note 2) | 2.0 |
| 6. Sesquiisostearic acid sorbitan | 1.5 |
| 7. Alkyl-modified branched polyether-modified silicone (note 3) | 2.0 |
| 8. Sorbitol sodium sulfate | 2.0 |
| 9. Chondroitin sulfate sodium | 1.0 |
| 10. Sodium hyaluronate | 0.5 |
| 11. Propylene glycol | 2.3 |
| 12. Preservative | 1.5 |
| 13. Vitamin E acetate | 0.1 |
| 14. Antioxidant | 0.5 |
| 15. Fragrance | 0.2 |
| 16. Purified water | 59.4 |
| Total | 100.0 |

(note 1): Product from Shin-Etsu Chemical Co., Ltd.; KF-54
(note 2): Product from Shin-Etsu Chemical Co., Ltd.; KF-7312J
(note 3): Product from Shin-Etsu Chemical Co., Ltd.; KF-6038

<Preparation of Cosmetic>
A: Components 1 to 7 and components 12 to 14 were mixed uniformly.
B: Components 8 to 11 and component 16 were mixed uniformly.
C: With agitation, product B was gradually added to product for emulsification; and component 15 was added thereinto to obtain a hair cream.

The hair cream thus obtained exhibited no greasiness, but smooth spreadability, water resistance, water repellency, perspiration resistance, and favorable cosmetic sustainability.

Example 21

Hair Cream

| (Components) | mass (%) |
|---|---|
| 1. Silicone gum solution (note 1) | 10.0 |
| 2. Silicone net-work resin dissolved product (note 2) | 10.0 |
| 3. Dissolved product of Synthesis Example 4 | 10.0 |
| 4. Tri-2-Glyceryl ethylhexanoate | 5.0 |
| 5. Vaseline | 5.0 |
| 6. Stearic acid | 1.5 |
| 7. Cetyl alcohol | 0.5 |
| 8. Polyglyceryl monooleate | 1.5 |
| 9. Glyceryl monostearate | 1.5 |
| 10. Polyether-modified silicone (note 3) | 0.5 |
| 11. 1,3-butylene glycol | 5.0 |
| 12. (acrylates/acrylic acid alkyl (C10-30)) crosspolymer (note 4) | 0.3 |
| 13. Triethanol amine | 0.3 |
| 14. Preservative | 0.5 |
| 15. Fragrance | 0.2 |
| 16. Purified water | 48.2 |
| Total | 100.0 |

(note 1): Product from Shin-Etsu Chemical Co., Ltd.; KF-9028
(note 2): Product from Shin-Etsu Chemical Co., Ltd.; KF-7312J
(note 3): Product from Shin-Etsu Chemical Co., Ltd.; KF-6011
(note 4): Product from Noveon Inc.; Pemulen TR-1

<Preparation of Cosmetic>
A: Components 1 to 10 and component 14 were dissolved by heating.
B: Components 11 to 13 and component 16 were mixed and heated.
C: With agitation, product A was gradually added to product B for emulsification; and component 15 was added thereinto, and then, after cooling, to obtain a hair cream.

The hair cream thus obtained exhibited smooth spreadability, luster and smoothness on hair, excellent setting effect on hair, water resistance, perspiration resistance, and favorable cosmetic sustainability.

Example 22

Moisturizing O/W Cream

| (Components) | mass (%) |
|---|---|
| 1. Dissolved product of Synthesis Example 7 | 4.0 |
| 2. Liquid paraffin | 4.5 |
| 3. Macadamia nut oil | 5.0 |
| 4. Dimethyl polysiloxane (viscosity 6 mm$^2$/s: 25° C.) | 5.0 |
| 5. Octyl para-methoxycinnamate | 5.0 |
| 6. Alkyl-modified branched polyglycerin-modified silicone (note 1) | 1.5 |
| 7. Propylene glycol | 8.0 |
| 8. Glycerin | 3.0 |
| 9. Preservative | 0.5 |
| 10. Fragrance | 0.2 |
| 11. Purified water | 63.3 |
| Total | 100.0 |

(note 1): Product from Shin-Etsu Chemical Co., Ltd.; KF-6105

<Preparation of Cosmetic>
A: Components 1 to 6 were mixed uniformly.
B: After Components 7 to 11 were mixed, the mixture was added to product A for emulsification to obtain a moisturizing O/W cream.

The moisturizing O/W cream thus obtained exhibited smooth spreadability, refreshing use feeling, and lasting moisturizing effect.

Example 23

O/W Emollient Cream

| (Components) | mass (%) |
|---|---|
| 1. Crosslinking dimethyl polysiloxane (note 1) | 7.0 |
| 2. Crosslinking dimethyl polysiloxane (note 2) | 30.0 |
| 3. Dissolved product of Synthesis Example 4 | 6.0 |
| 4. Decamethyl cyclopentasiloxane | 5.0 |
| 5. 1,3-butylene glycol | 4.0 |
| 6. Branched polyglycerin-modified silicone (note 3) | 0.6 |
| 7. Branched polyglycerin-modified silicone (note 4) | 0.3 |
| 8. (acrylamide/acryloyldimethyl taurine Na) copolymer (note 5) | 0.6 |
| 9. Acrylic acid dimethyltaurine ammonium/VP copolymer (note 6) | 0.7 |
| 10. Sodium chloride | 0.1 |
| 11. Purified water | 45.7 |
| Total | 100.0 |

(note 1): Product from Shin-Etsu Chemical Co., Ltd.; KSG-15
(note 2): Product from Shin-Etsu Chemical Co., Ltd.; KSG-16
(note 3): Product from Shin-Etsu Chemical Co., Ltd.; KF-6104
(note 4): Product from Shin-Etsu Chemical Co., Ltd.; KF-6100
(note 5): Product from Seppic Inc.; SIMULGEL 600
(note 6): Product from Clariant Corporation; Aristoflex AVC <Preparation of Cosmetic>
A: Components 1 to 4 were mixed uniformly.
B: Components 5 to 11 were mixed uniformly.
C: With agitation, product A was gradually added to product B to be mixed to obtain an O/W emollient cream.

The O/W emollient cream thus obtained exhibited no greasiness, but smooth foam touch, smooth spreadability and lasting skin-protecting effect.

Example 24

Hand Cream

| (Components) | mass (%) |
|---|---|
| 1. Decamethyl cyclopentasiloxane | 25.0 |
| 2. Dissolved product of Synthesis Example 4 | 10.0 |
| 3. Liquid paraffin | 5.0 |
| 4. Amino-modified silicone gum dissolved product (note 1) | 8.0 |
| 5. Branched polyether-modified silicone (note 2) | 2.0 |
| 6. Hybrid silicone composite powder (note 3) | 2.5 |
| 7. Distearyldimethyl ammonium chloride | 0.8 |
| 8. Vitamin E acetate | 0.1 |
| 9. Polyethylene glycol 400 | 1.0 |
| 10. Glycerin | 10.0 |
| 11. Aluminum magnesium silicate | 1.2 |
| 12. Preservative | 0.5 |
| 13. Fragrance | 0.2 |
| 14. Purified water | 33.7 |
| Total | 100.0 |

(note 1): Product from Shin-Etsu Chemical Co., Ltd.; KF-8108
(note 2): Product from Shin-Etsu Chemical Co., Ltd.; KF-6028P
(note 3): Product from Shin-Etsu Chemical Co., Ltd.; KSP-102

<Preparation of Cosmetic>
A: Components 1 to 8 and component 12 were mixed uniformly.
B: Components 9 to 11 and component 14 were mixed uniformly.
C: With agitation, product B was added to product A for emulsification; and component 13 was added thereinto to obtain a hand cream.

The thus obtained exhibited no greasiness, but smooth foam touch, smooth spreadability, and lasting skin-protecting effect.

Example 25

O/W Cream

| (Components) | mass (%) |
|---|---|
| 1. Dimethyl polysiloxane (6cs) | 7.0 |
| 2. Stearyl-modified acrylic silicone resin (note 1) | 8.0 |
| 3. Dissolved product of Synthesis Example 7 | 5.0 |
| 4. Glyceryl triisostearate | 10.0 |
| 5. Cetanol | 1.0 |
| 6. Stearic acid | 3.0 |
| 7. Glyceryl monostearate | 1.5 |
| 8. Sorbitan sesquioleate | 0.5 |
| 9. Monooleic acidpolyoxyethylene sorbitan | 1.0 |
| 10. Sodium hydroxide (1% by mass solution) | 10.0 |
| 11. 1,3-butylene glycol | 5.0 |
| 12. Preservative | 0.5 |
| 13. Fragrance | 0.2 |
| 14. Purified water | 47.3 |
| Total | 100.0 |

(note 1): Product from Shin-Etsu Chemical Co., Ltd.; KP-561P

<Preparation of Cosmetic>
A: Components 1 to 9 were mixed by heating.
B: Components 10 to 12 and component 14 were mixed and heated.

C: With agitation, product B was gradually added to product A for emulsification; and component 13 was added thereinto, and then, after cooling, to obtain an O/W cream.

The O/W cream thus obtained exhibited neither stickiness nor greasinesss, but smooth foam touch, smooth spreadability, and refreshing use feeling.

Example 26

O/W Cream

| (Components) | mass (%) |
|---|---|
| 1. Polyglyceryl monooleate | 1.0 |
| 2. Cetyl alcohol | 0.5 |
| 3. Stearic acid | 1.0 |
| 4. Glyceryl monostearate | 1.0 |
| 5. Dissolved product of Synthesis Example 5 | 2.0 |
| 6. Macadamia nut oil | 9.0 |
| 7. Crosslinking dimethyl polysiloxane (note 1) | 0.5 |
| 8. (acrylates/acrylic acid alkyl (C10-30)) crosspolymer (note 2) | 0.2 |
| 9. Methyl cellulose | 0.1 |
| 10. Triethanol amine | 0.2 |
| 11. 1,3-butylene glycol | 7.0 |
| 12. Preservative | 0.5 |
| 13. Fragrance | 0.2 |
| 14. Purified water | 76.8 |
| Total | 100.0 |

(note 1): Product from Shin-Etsu Chemical Co., Ltd.; KSG-16
(note 2): Product from Noveon Inc.; Pemulen TR-1

<Preparation of Cosmetic>
A: Components 1 to 7 were mixed uniformly by heating.
B: Components 8 to 12 and component 14 were mixed and heated.
C: With agitation, product B was gradually added to product A for emulsification, to which component 13 was added thereinto, and then, after cooling, to obtain an O/W cream.

The O/W cream thus obtained exhibited neither stickiness nor greasiness, but smooth foam touch, smooth spreadability, and lasting skin freshness.

Example 27

Antiperspirant

| (Components) | mass (%) |
|---|---|
| 1. Crosslinking polyether-modified silicone (note 1) | 7.0 |
| 2. Dissolved product of Synthesis Example 4 | 8.0 |
| 3. Decamethyl cyclopentasiloxane | 9.0 |
| 4. 1,3-butylene glycol | 5.0 |
| 5. Sodium citrate | 0.2 |
| 6. Glycine salt of aluminum zirconium hydrate tetrachloride | 20.0 |
| 7. Purified water | 50.8 |
| Total | 100.0 |

(note 1): Product from Shin-Etsu Chemical Co., Ltd.; KSG-210

<Preparation of Cosmetic>
A: Components 1 to 3 were mixed uniformly.
B: Components 4 to 7 were mixed uniformly.
C: With agitation, product B was gradually added to product A for emulsification to obtain an antiperspirant.

The antiperspirant thus obtained exhibited smooth spreadability, and favorable cosmetic sustainability of non-skin-lightening and antiperspirant effects.

Example 28

Wrinkle Concealer

| (Components) | mass (%) |
|---|---|
| 1. Crosslinking polyether-modified silicone (note 1) | 5.0 |
| 2. Crosslinking dimethyl polysiloxane (note 2) | 55.0 |
| 3. Dissolved product of Synthesis Example 5 | 15.0 |
| 4. Decamethyl cyclopentasiloxane | 8.0 |
| 5. Hybrid silicone composite powder (note 3) | 12.0 |
| 6. Silicone gum solution (note 4) | 5.0 |
| Total | 100.0 |

(note 1): Product from Shin-Etsu Chemical Co., Ltd.; KSG-210
(note 2): Product from Shin-Etsu Chemical Co., Ltd.; KSG-15
(note 3): Product from Shin-Etsu Chemical Co., Ltd.; KSP-101
(note 4): Product from Shin-Etsu Chemical Co., Ltd.; KF-9028

<Preparation of Cosmetic>
A: Components 1 to 6 were mixed uniformly to obtain a wrinkle concealer.

The wrinkle concealer thus obtained exhibited neither stickiness nor greasiness, but smooth foam touch, smooth spreadability, and lasting concealing effect.

Example 29

Cleansing Cream

| (Components) | mass (%) |
|---|---|
| 1. Dimethyl polysiloxane (6cs) | 5.0 |
| 2. Methyl phenyl polysiloxane (note 1) | 5.0 |
| 3. Liquid paraffin | 5.0 |
| 4. Jojoba oil | 2.0 |
| 5. Dissolved product of Synthesis Example 7 | 4.0 |
| 6. Branched polyether-modified silicone (note 2) | 2.0 |
| 7. Dextrin fatty ester | 0.8 |
| 8. Monoaluminum stearate salt | 0.2 |
| 9. Aluminum chloride | 1.0 |
| 10. Glycerin | 10.0 |
| 11. Preservative | 0.5 |
| 12. Fragrance | 0.2 |
| 13. Purified water | 64.3 |
| Total | 100.0 |

(note 1): Product from Shin-Etsu Chemical Co., Ltd.; KF-56
(note 2): Product from Shin-Etsu Chemical Co., Ltd.; KF-6028

<Preparation of Cosmetic>
A: Components 1 to 8 were mixed by heating.
B: Components 9 to 11 and component 13 were mixed by heating.
C: With agitation, product B was gradually added to product A for emulsification; and component 12 was added thereinto, and then, after cooling, to obtain a cleansing cream.

The cleansing cream thus obtained exhibited smooth spreadability, moisturizing texture, excellent freshness, and refreshing use feeling.

Example 30

Transparent Cleansing Cream Lotion

| (Components) | mass (%) |
|---|---|
| 1. Decamethyl cyclopentasiloxane | 50.8 |
| 2. Dissolved product of Synthesis Example 4 | 5.0 |
| 3. Neopentyl glycol dioctanoate | 6.0 |
| 4. silica | 0.2 |
| 5. 1,3-butylene glycol | 5.0 |
| 6. Glycerin | 6.0 |
| 7. Polyether-modified silicone (note 1) | 5.0 |
| 8. Polyether-modified silicone (note 2) | 3.0 |
| 9. PEG-60 hydrogenated castor oil | 2.0 |
| 10. Purified water | 17.0 |
| Total | 100.0 |

(note 1): Product from Shin-Etsu Chemical Co., Ltd.; KF-6011
(note 2): Product from Shin-Etsu Chemical Co., Ltd.; KF-6013

<Preparation of Cosmetic>
A: Components 1 to 4 were mixed uniformly.
B: Components 5 to 10 were mixed uniformly.
C: With agitation, product A was gradually added to product B for emulsification to obtain a transparent cleansing cream lotion.

The transparent cleansing cream lotion thus obtained exhibited smooth spreadability, moisturizing texture, fresh feeling of use, and high cleansing cream effect.

Example 31

W/O Rouge

| (Components) | mass (%) |
|---|---|
| 1. Acrylic silicone resin dissolved product (note 1) | 10.0 |
| 2. Stearyl-modified acrylic silicone resin (note 2) | 2.0 |
| 3. Branched polyether-modified silicone (note 3) | 1.5 |
| 4. Decamethyl cyclopentasiloxane | 15.0 |
| 5. Glyceryl triisostearate | 3.0 |
| 6. Dissolved product of Synthesis Example 5 | 5.0 |
| 7. Dimethyldistearyl ammonium hectorite | 1.5 |
| 8. Spherical shapenylon | 3.0 |
| 9. Talc | 4.0 |
| 10. Rouge pigment (acrylic silicone-treated) (note 4) | 20.0 |
| 11. Alcohol | 5.0 |
| 12. Fragrance | 0.2 |
| 13. Purified water | 29.8 |
| Total | 100.0 |

(note 1): Product from Shin-Etsu Chemical Co., Ltd.; KP-545
(note 2): Product from Shin-Etsu Chemical Co., Ltd.; KP-561P
(note 3): Product from Shin-Etsu Chemical Co., Ltd.; KF-6028P
(note 4): Product from Shin-Etsu Chemical Co., Ltd.; KP-574-treated <Preparation of Cosmetic>
A: Components 1 to 7 were mixed by heating.
B: Components 8 to 10 and component 12 were mixed uniformly; and mixed with product A.
C: Component 11 and 13 were mixed.
D: With agitation, product C was gradually added to product B for emulsification to obtain a W/O rouge.

The W/O rouge thus obtained exhibited neither stickiness nor greasiness, but smooth spreadability, excellent adhesivity, and favorable cosmetic sustainability as well.

Example 32

W/O Facial Liquid Foundation

| (Components) | mass (%) |
|---|---|
| 1. Crosslinking polyether-modified silicone (note 1) | 3.0 |
| 2. Crosslinking dimethyl polysiloxane (note2) | 5.0 |
| 3. Branched polyether-modified silicone (note 3) | 2.0 |
| 4. Decamethyl cyclopentasiloxane | 20.0 |
| 5. Cetyl isooctanoate | 5.0 |
| 6. Dissolved product of Synthesis Example 4 | 10.0 |
| 7. Dimethyldistearyl ammonium hectorite | 1.2 |
| 8. Foundation-pigment (silicone-treated) (note 4) | 14.0 |
| 9. Acrylic silicone resin dissolved product (note 5) | 10.0 |
| 10. 1,3-butylene glycol | 5.0 |
| 11. Xanthan gum | 0.1 |
| 12. Sodium citrate | 0.2 |
| 13. Sodium chloride | 0.5 |
| 14. Preservative | 0.5 |
| 15. Fragrance | 0.2 |
| 16. Purified water | 23.3 |
| Total | 100.0 |

(note 1): Product from Shin-Etsu Chemical Co., Ltd.; KSG-210
(note 2): Product from Shin-Etsu Chemical Co., Ltd.; KSG-15
(note 3): Product from Shin-Etsu Chemical Co., Ltd.; KF-6028P
(note 4): Product from Shin-Etsu Chemical Co., Ltd.; KF-9909-treated
(note 5): Product from Shin-Etsu Chemical Co., Ltd.; KP-575

<Preparation of Cosmetic>
A: Part of component 4 and component 9 were mixed; and component 8 was uniformly dispersed.
B: Components 1 to 3, and a remainder of component 4, and components 5 to 7 were mixed uniformly.
C: Components 10 to 14 and component 16 were mixed uniformly.
D: With agitation, product C was gradually added to product B for emulsification; and product A and component 15 were added thereinto to obtain a W/O facial liquid foundation.

The W/O facial liquid foundation thus obtained exhibited neither stickiness nor greasiness, but smooth spreadability, favorable cosmetic sustainability, and no secondary adhesion.

Example 33

W/O Cream

| (Components) | mass (%) |
|---|---|
| 1. Crosslinking alkyl and polyether-modified silicone (note 1) | 3.0 |
| 2. Crosslinking alkyl-modified dimethyl polysiloxane (note 2) | 4.0 |
| 3. Alkyl-modified branched polyether-modified silicone (note 3) | 1.0 |
| 4. Meadowfoam seed oil | 3.5 |
| 5. Jojoba oil | 2.5 |
| 6. Macadamia nut oil | 5.0 |
| 7. Dissolved product of Synthesis Example 7 | 7.5 |
| 8. Hybrid silicone composite powder (note 4) | 3.0 |
| 9. 1,3-butylene glycol | 8.0 |
| 10. Glycine | 3.0 |
| 11. Sodium citrate | 0.2 |
| 12. Sodium chloride | 0.5 |
| 13. Preservative | 0.5 |

-continued

| (Components) | mass (%) |
|---|---|
| 14. Fragrance | 0.2 |
| 15. Purified water | 58.1 |
| Total | 100.0 |

(note 1): Product from Shin-Etsu Chemical Co., Ltd.; KSG-340
(note 2): Product from Shin-Etsu Chemical Co., Ltd.; KSG-44
(note 3): Product from Shin-Etsu Chemical Co., Ltd.; KF-6038
(note 4): Product from Shin-Etsu Chemical Co., Ltd.; KSP-100

<Preparation of Cosmetic>
A: Components 1 to 8 were mixed uniformly.
B: Components 9 to 13 and component 15 were mixed uniformly.
C: With agitation, product B was gradually added to product A for emulsification; and component 14 was added thereinto to obtain a W/O cream.

The W/O cream thus obtained exhibited neither stickiness nor greasiness, but lasting skin moisturizing texture.

Example 34

Cuticle Coat

| (Components) | mass (%) |
|---|---|
| 1. Polyether-modified silicone (note 1) | 3.0 |
| 2. Polyether-modified silicone (note 2) | 2.0 |
| 3. PEG-40 hydrogenated cured castor oil | 1.0 |
| 4. Dissolved product of Synthesis Example 4 | 3.0 |
| 5. Silicone gum dissolved product (note 3) | 40.0 |
| 6. Decamethyl cyclopentasiloxane | 40.0 |
| 7. Alcohol | 4.3 |
| 8. Preservative | 0.5 |
| 9. Fragrance | 0.2 |
| 10. Purified water | 6.0 |
| Total | 100.0 |

(note 1): Product from Shin-Etsu Chemical Co., Ltd.; KF-6011
(note 2): Product from Shin-Etsu Chemical Co., Ltd.; KF-6013
(note 3): Product from Shin-Etsu Chemical Co., Ltd.; KF-9028

<Preparation of Cosmetic>
A: Components 1 to 3 and components 7 to 10 were mixed uniformly.
B: Components 4 to 6 were mixed uniformly.
C: With agitation, product B was added to product A for emulsification to obtain a cuticle coat.

The cuticle coat thus obtained exhibited smooth spreadability, an effect of suppressing a dry feeling of the hair, and luster and smoothness.

Example 35

Hair Treatment

| (Components) | mass (%) |
|---|---|
| 1. Silicone gum dissolved product (note 1) | 5.0 |
| 2. Diphenyl dimethicone (note 2) | 4.0 |
| 3. Dissolved product of Synthesis Example 6 | 1.0 |
| 4. Cetyl octanoate | 1.0 |
| 5. Cetyl alcohol | 0.5 |
| 6. Polyether-modified silicone (note 3) | 1.0 |

-continued

| (Components) | mass (%) |
|---|---|
| 7. PEG-60 hydrogenated cured castor oil | 1.0 |
| 8. Glyceryl monostearate | 0.5 |
| 9. Carboxy vinyl polymer (1% by mass solution) | 25.0 |
| 10. Xanthan gum (1% by mass solution) | 7.0 |
| 11. 1,3-butylene glycol | 5.0 |
| 12. Alcohol | 7.0 |
| 13. Preservative | 0.5 |
| 14. Fragrance | 0.2 |
| 15. Purified water | 41.3 |
| Total | 100.0 |

(note 1): Product from Shin-Etsu Chemical Co., Ltd.; MK-15H
(note 2): Product from Shin-Etsu Chemical Co., Ltd.; KF-54
(note 3): Product from Shin-Etsu Chemical Co., Ltd.; KF-6013

<Preparation of Cosmetic>
A: Components 1 to 8 were dissolved by heating.
B: Components 11 to 15 were dissolved by heating.
C: With agitation, product B was added to product A for emulsification; and components 9 and 10 were further added thereinto to obtain a hair treatment.

The hair treatment thus obtained exhibited smooth spreadability, and luster and smoothness on the hair.

Example 36

Nail Enamel

| (Components) | mass (%) |
|---|---|
| 1. Dissolved product of Synthesis Example 6 | 35.0 |
| 2. Methyltrimethicone (note 1) | 5.0 |
| 3. Nitrocellulose | 3.0 |
| 4. Camphor | 0.5 |
| 5. Acetyl tributyl citrate | 1.0 |
| 6. Dimethyldistearyl ammonium hectorite | 0.5 |
| 7. Butyl acetate | 30.0 |
| 8. Ethyl acetate | 13.0 |
| 9. Isopropyl alcohol | 5.0 |
| 10. Coloring pigment | 7.0 |
| Total | 100.0 |

(note 1): Product from Shin-Etsu Chemical Co., Ltd.; TMF-1.5

<Preparation of Cosmetic>
A: Components 7 to 9 were mixed; and components 4 to 6 were added thereinto and mixed uniformly.
B: Components 1 to 3 were added to product A and mixed.
C: Component 10 was added to product B to be mixed to obtain a nail enamel.

The nail enamel obtained exhibited smooth spreadability, luster on the nails and excellent cosmetic sustainability.

Example 37

Nail Enamel Overcoat

| (Components) | mass (%) |
|---|---|
| 1. Dissolved product of Synthesis Example 6 | 6.0 |
| 2. Nitrocellulose | 17.0 |
| 3. Alkyd resin | 4.0 |
| 4. Acetyl triethyl citrate | 5.0 |
| 5. Butyl acetate | 29.0 |
| 6. Ethyl acetate | 25.0 |

| (Components) | mass (%) |
|---|---|
| 7. Isopropyl alcohol | 3.0 |
| 8. n-butyl alcohol | 1.0 |
| 9. Toluene | 10.0 |
| Total | 100.0 |

<Preparation of Cosmetic>
A: Components 5 to 9 were mixed; and component 4 was added thereinto and mixed uniformly.
B: Components 1 to 3 were added to product A to be mixed to obtain a nail enamel overcoat.

The nail enamel overcoat thus obtained exhibited smooth spreadability, more luster of enamel, and favorable cosmetic sustainability.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

What is claimed is:

1. A cosmetic comprising a sugar compound obtained by reacting a hydroxyl group of a saccharide, an isocyanate group-containing organopolysiloxane represented by the following general formula (1), and an isocyanate group-containing organic compound represented by the following general formula (2), $$O=C=N-(CH_2)_n-Si \begin{matrix} R_a^1 \\ | \\ \phantom{Si} \\ \end{matrix} \left( O-Si\begin{matrix} R^2 \\ | \\ | \\ R^4 \end{matrix} R^3 \right)_{3-a} \quad (1)$$

wherein $R^1$, $R^2$, $R^3$, and $R^4$ independently represent a group selected from the group consisting of an alkyl group having 1 to 8 carbon atoms, a fluorine-substituted alkyl group having 1 to 8 carbon atoms, and an aryl group having 6 to 12 carbon atoms, with "n" representing an integer of 1 to 10 and "a" representing an integer of 0 to 3, $$O=C=N-R^5 \quad (2)$$

wherein $R^5$ represents a group selected from the group consisting of an alkyl group having 3 to 30 carbon atoms, an aryl group having 6 to 30 carbon atoms, an aralkyl group having 6 to 30 carbon atoms, and an organic group represented by the following general formula (3), $$-R^6-X-R^7 \quad (3)$$

wherein $R^6$ represents a divalent hydrocarbon group having 2 to 20 carbon atoms; and $R^7$ represents an alkyl group having 1 to 30 carbon atoms, with "X" representing a group represented by —NHCONH— or NHCOO—.

2. The cosmetic according to claim 1, wherein the sugar compound is reacted with the isocyanate group-containing organopolysiloxane and the isocyanate group-containing organic compound, with a molar ratio being in a range of 0.03 to 0.7 per mole of a hydroxyl group of the saccharide.

3. The cosmetic according to claim 1, wherein the saccharide is a pullulan or a cellulose.

4. The cosmetic according to claim 2, wherein the saccharide is a pullulan or a cellulose.

5. The cosmetic according to claim 1, wherein "n" represents an integer of 3, and $R^1$, $R^2$, $R^3$ and $R^4$ represent a methyl group in the general formula (1).

6. The cosmetic according to claim 2, wherein "n" represents an integer of 3, and $R^1$, $R^2$, $R^3$ and $R^4$ represent a methyl group in the general formula (1).

7. The cosmetic according to claim 3, wherein "n" represents an integer of 3, and $R^1$, $R^2$, $R^3$ and $R^4$ represent a methyl group in the general formula (1).

8. The cosmetic according to claim 4, wherein "n" represents an integer of 3, and $R^1$, $R^2$, $R^3$ and $R^4$ represent a methyl group in the general formula (1).

9. The cosmetic according to claim 1, wherein $R^5$ represents an alkyl group having 3 to 30 carbon atoms in the general formula (2).

10. The cosmetic according to claim 2, wherein $R^5$ represents an alkyl group having 3 to 30 carbon atoms in the general formula (2).

11. The cosmetic according to claim 3, wherein $R^5$ represents an alkyl group having 3 to 30 carbon atoms in the general formula (2).

12. The cosmetic according to claim 4, wherein $R^5$ represents an alkyl group having 3 to 30 carbon atoms in the general formula (2).

13. The cosmetic according to claim 5, wherein $R^5$ represents an alkyl group having 3 to 30 carbon atoms in the general formula (2).

14. The cosmetic according to claim 6, wherein $R^5$ represents an alkyl group having 3 to 30 carbon atoms in the general formula (2).

15. The cosmetic according to claim 7, wherein $R^5$ represents an alkyl group having 3 to 30 carbon atoms in the general formula (2).

16. The cosmetic according to claim 8, wherein $R^5$ represents an alkyl group having 3 to 30 carbon atoms in the general formula (2).

17. The cosmetic according to claim 1, wherein the cosmetic contains the sugar compound, with an amount thereof being 0.05 to 40% by mass, relative to a total amount of the cosmetic.

18. The cosmetic according to claim 1, wherein the cosmetic further contains water and is in a form of an emulsion.

19. The cosmetic according to claim 1, wherein the cosmetic further contains any of a silicone oil, a hydrocarbon oil, a glycol, an ester oil, a glyceride oil, a UV-absorber, or a mixture thereof.

20. The cosmetic according to claim 1, wherein the cosmetic further contains a powder and is in a form of a liquid, a paste, or a solid, with the powder being dispersed therein.

* * * * *